United States Patent
Tsuji et al.

(10) Patent No.: US 6,664,110 B1
(45) Date of Patent: Dec. 16, 2003

(54) ERYTHROBLAST DIAGNOSTIC FLOW-CYTOMETRY METHOD AND REAGENTS

(75) Inventors: Tomohiro Tsuji, Himeji (JP); Takashi Sakata, Kakogawa (JP); Yoshiro Ikeuchi, Himeji (JP); Shin'ichiro Oguni, Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 09/207,995

(22) Filed: Dec. 9, 1998

(30) Foreign Application Priority Data

Nov. 27, 1998 (JP) ............................. 10-336916

(51) Int. Cl.⁷ .............................................. G01N 31/00
(52) U.S. Cl. ........................... 436/63; 436/10; 436/172; 436/17
(58) Field of Search ............................ 436/10, 63, 172, 436/17

(56) References Cited

U.S. PATENT DOCUMENTS

| 5,175,109 A | | 12/1992 | Sakata et al. | |
|---|---|---|---|---|
| 5,264,369 A | * | 11/1993 | Sakata et al. | 436/63 |
| 5,438,003 A | * | 8/1995 | Colella et al. | 436/63 |
| 5,733,784 A | * | 3/1998 | Studholme et al. | 436/63 |
| 5,821,127 A | * | 10/1998 | Akai et al. | 436/10 |
| 5,891,731 A | * | 4/1999 | Akai et al. | 436/10 |
| 5,891,733 A | * | 4/1999 | Inoue | 436/63 |
| 5,945,340 A | * | 8/1999 | Francis et al. | 436/10 |
| 5,994,138 A | * | 11/1999 | Veriac | 436/10 |
| 6,004,816 A | * | 12/1999 | Mizukami et al. | 436/10 |

FOREIGN PATENT DOCUMENTS

| EP | 0 499 693 A2 | 8/1992 |
|---|---|---|
| EP | 0 872 734 A1 | 10/1998 |

* cited by examiner

*Primary Examiner*—Jill Warden
*Assistant Examiner*—LaToya I Cross
(74) *Attorney, Agent, or Firm*—Shinjyu Global IP

(57) ABSTRACT

Reagents and a method for simple and rapid discrimination and counting of erythroblasts in peripheral blood or circulatory system-related samples accurately with high precision is disclosed. The reagents include a hemolytic agent for dissolving erythrocytes in a body fluid sample and for conditioning leukocytes and erythroblasts in the sample to be suitable for staining, and including at least one fluorescent dye selected to stain leukocytes and erythroblasts differentially. When the selected fluorescent dye is mixed with the sample, a detectable difference in fluorescence intensity at least between leukocytes and erythroblasts arises under laser illumination in flow cytometric analysis. The reagents further include surfactant added to the hemolytic agent, selected to enable flow cytometric discrimination of erythroblasts in the body fluid sample by their maturation stages.

25 Claims, 5 Drawing Sheets

ERYTHROBLAST DIAGNOSTIC FLOW-CYTOMETRY METHOD AND REAGENTS

BACKGROUND OF THE INVENTION

1. Technical Field

The present invention relates to flow-cytometric diagnosis of formed elements of blood; in particular the invention relates to discrimination and counting of erythroblasts from peripheral blood or other body fluid samples by flow cytometry.

2. Description of Related Art

In the field of clinical examination, sorting and counting of erythroblasts can yield vital information in the diagnosis of disease.

Erythropoiesis is a process of the bone marrow, and normally erythroblasts, prior to their release into circulation as reticulocytes in the final stage of maturation into red blood cells, are not present in the peripheral blood. Consequently, the appearance in the peripheral blood of erythroblasts in any of the distinguishable erythropoietic stages prior to becoming reticulocytes indicates the possibility of the presence of disease, such as acute myelocytic leukemia, hemolytic anemia, iron deficiency anemia and pernicious anemia. Accordingly, erythroblast sorting and counting can be extremely useful in diagnosing these sorts of diseases.

Conventionally in counting and sorting erythroblasts, generally blood smears are prepared which are then suitably stained for counting and sorting through microscopic observation.

On the other hand, various fully automated leukocyte sorter/counter devices that apply flow cytometric principles are available. "Flow Cytometers—History and Measurement Principle," *Sysmex Journal International*, Vol. 6 No. 1 (1996) is an introduction to flow cytometry as applicable to the present invention, and is herein incorporated by reference.

Wherein erythroblasts have appeared in the peripheral blood, however, results output from flow cytometric devices and analyzed diagrammatically only suggest, by abnormal "flags," (indicating unusual plots from the flow cytometric data) the possibility of the presence of erythroblasts, and do not enable accurate erythroblast sorting/counting. Such flags often turn out to be false positive results.

Furthermore, apart from the foregoing, Japanese Laid-Open Pat. No. 4-268453 (1992), and U.S. Pat. No. 5,559,037 disclose erythroblast sorting/counting methods.

Either of these are methods by which erythroblasts are assayed by treating samples with a suitable hemolytic agent that disables only cell membranes of erythrocytes (confers dye permeability to the cell membranes) and with a solvent that does not injure cell membranes of leukocytes (does not confer dye permeability to the cell membranes), and afterwards (or at the same time) staining with a fluorescent dye only the erythroblasts whose cell membranes have been damaged, then discriminating erythroblasts from leukocytes by measuring fluorescence intensity.

Wherein fresh blood is used immediately after the sample is taken, accurate measurements are possible with these methods. With the elapse of time after a blood sample is taken, however, not only erythroblast but also leukocyte cell membranes are easily injured, and a likely portion of the leukocytes will get stained by the fluorescent dye because their cell membranes have been damaged prior to the mixing in of hemolytic agent. There is a problem in particular wherein lymphocyte cells are injured, in that it is difficult to discriminate injured lymphocytes distinctly from erythroblasts, such that erythroblasts cannot be sorted and counted accurately.

With some samples in which lymphoblasts appear, which are close in size to erythroblasts, or with samples from chemotheraphy patients in which cell membranes of leukocytes are liable to be disabled by the hemolytic agent, accurate erythroblast counting/sorting is difficult even right after the blood is drawn.

SUMMARY OF THE INVENTION

An object of the present invention is to discriminate and count erythroblasts in peripheral blood or circulatory system-related samples accurately with high precision, even with samples wherein post-sample draw time has elapsed, or wherein easily damaged leukocytes are present.

The present invention provides reagents for discriminating and counting erythroblasts, including a hemolytic agent for dissolving erythrocytes in a body fluid sample and for conditioning leukocytes and erythroblasts in the sample to be suitable for staining, and including at least one fluorescent dye selected to stain leukocytes and erythroblasts differentially. When the selected fluorescent dye is mixed with the sample, a detectable difference in fluorescence intensity at least between leukocytes and erythroblasts arises under laser illumination in flow cytometric analysis.

The reagents provided by the present invention further include surfactant added to the hemolytic agent, selected to enable flow cytometric discrimination of erythroblasts in the body fluid sample by their maturation stages.

Furthermore, the present invention is a method of flow-cytometrically assaying body fluid samples utilizing reagents as mentioned above to discriminate and count erythroblasts in the samples.

The method includes the preparatory steps of: (a) mixing the body fluid sample with a hemolytic agent selected for dissolving erythrocytes within body fluid samples to an extent that does not interfere with the flow-cytometric assay, and for conditioning leukocytes and erythroblasts in the assay sample to be suitable for staining, and (b) staining leukocytes and erythroblasts in the sample as prepared in said step (a) by mixing the sample with at least one of the fluorescent dyes selected to stain leukocytes and erythroblasts differentially; and the method further includes the steps of: (c) flow cytometrically assaying the sample as prepared in said step (b) by measuring at least one scattered light parameter and at least one fluorescence parameter, and (d) discriminating and counting erythroblasts utilizing intensity differences in scattered light and in fluorescence as measured in step (c).

The foregoing and other objects, features, aspects and advantages of the present invention will become more apparent from the following detailed description in conjunction with the accompanying drawings.

DETAILED DESCRIPTION OF THE PREFERRED EMBODIMENTS

Figure 1:
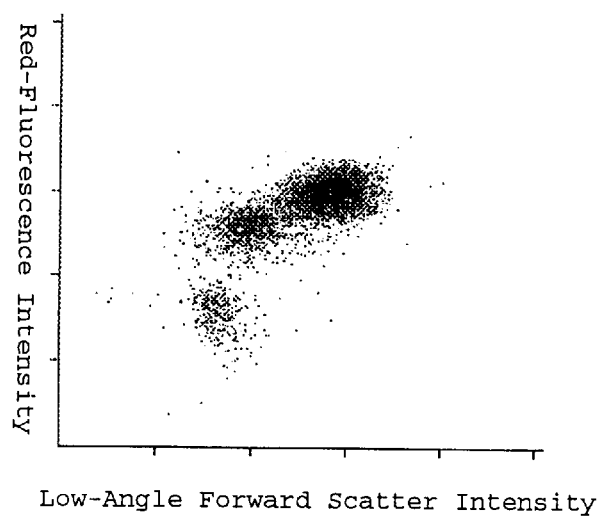
FIG. 1 is an example of a red fluorescence intensity/low-angle forward scatter intensity scattergram for a blood sample assayed utilizing the method of the present invention.

Assay samples in the present invention are body fluids containing leukocytes and erythroblasts, and as such include samples from the blood peripheral circulation, bone marrow fluid, urine or samples obtained via apheresis.

A method for discriminating and counting erythroblasts in accordance with the present invention, employs a hemolytic agent selected for dissolving erythrocytes in body fluid sample to an extent such that the hemolytic agent does not interfere with flow cytometric assay, and for conditioning leukocytes and erythroblasts in the body fluid sample to be suitable for staining.

A suitable hemolytic agent is, for example, an aqueous solution having a pH of about 2.0 to 5.0 and an osmotic pressure of about 100 mOsm/kg or less. Such a hemolytic agent according to the invention further may contain surfactant in a concentration in the range of 10 to 10,000 mg/l.

Principal objects of the inventive method are to dissolve erythrocytes, which ordinarily are present in a concentration 1000 times that of leukocytes and interfere with assaying of erythroblasts, and to stain body fluid sample leukocytes and erythroblasts differentially, wherein said fluorescent dye is selected to produce a difference detectable by flow cytometry in fluorescence intensity between the leukocytes and erythroblasts.

Although there are slight individual differences, ordinarily rupturing will occur in the cell membranes of erythrocytes in solution at an osmotic pressure of 150 mOsm/kg or less, and the intracellular hemoglobin will flow out (i.e., hemolysis occurs), such that the cells become optically transparent "ghosts." Optically transparent erythrocytes accordingly do not hinder assaying of leukocytes and erythroblasts. Hemolysis proceeds even faster the lower the osmotic pressure and pH value of the solution, and the greater the amount of surfactant. Taking into consideration individual differences in erythrocytes, in the present invention the hemolytic agent is employed at an osmotic pressure of 100 mOsm/kg or less. To achieve this osmotic pressure, the hemolytic agent can be adjusted by an electrolyte such as NaCl or KCl, a sugar or a buffer as described below.

Wherein the pH is too low, not only erythrocytes but also leukocytes and erythroblasts are subject to excessive hindrance, and therefore it becomes difficult to obtain a below-described analyzable difference in fluorescence intensity.

In order that erythrocytic hemolysis be carried out efficiently, it is preferable that the pH be in the acidic end. Especially preferable is a pH of 2.0–5.0, and more preferably a pH of 2.5–4.5 is selected.

Likewise, excessively high surfactant concentration in the hemolytic agent handicaps flow cytometric assay based on the below described difference in fluorescence intensity, not only of erythrocytes, but also of leukocytes and erythroblasts.

In order to enable counting and discriminating of erythroblasts by maturation stage, it is suitable to make the concentration of surfactant 10–10,000 mg/l. It is more suitable to select a concentration of about 100–5,000 mg/l. This accordingly enables sorting of the maturation stages present in the erythroblast population into at least two groups.

It is preferable to use a buffer to maintain the solution at constant pH, and a buffer having a $pK_a$ that sets the pH in the vicinity of ±2.0 can be employed. For example the buffer can be selected from citric acid, malic acid, diglycolic acid, and malonic acid.

Furthermore, a hemolytic agent which contains intramolecularly at least either an organic acid having at least one aromatic ring, or its salt, dissolves erythrocytes more efficiently (i.e., in a shorter period of time). Examples of a preferable organic acid or its salt include salicylic acid, sodium salicylate and phthalic acid.

Under these conditions, rupturing of the cell membrane and hemolysis of erythroblasts will also occur likewise as with erythrocytes, however, properties of the erythroblast nuclei nearly the same as those of living cells are retained.

On the other hand, damage to leukocyte cell membranes is not definite, and optically under microscopic observation no notable difference from living cells could be recognized.

A preferable hemolytic agent for the present invention dissolves erythrocytes at hypotonic osmotic pressure and contains a dissolve-resistant dye solublizer, and surfactant for the purpose of preventing ghost erythrocyte agglutination, preventing platelet agglutination and for promoting ghost shrinkage and erythrocytic hemolysis.

As noted above, the presence of a great quantity of surfactant in the hemolytic agent is a problem, in particular because excess surfactant changes erythroblast nuclear properties and lessens the difference in fluorescence intensity between erythroblasts and leukocytes as defined below.

Consequently for the hemolytic agent employed in the present invention, the surfactant is adjusted so as not to lessen the difference in fluorescence intensity between erythroblasts and leukocytes, and distinct from conventional hemolytic agents, the surfactant does not contain ingredients that dissolve cell components.

The foregoing conditions for the flow-cytometric assaying reagents and method of the present invention, unanticipatedly gave rise to a distinct difference, conventionally considered impossible, in fluorescence intensity between erythroblasts and leukocytes, and furthermore enabled the discrimination and counting of erythroblasts by maturation stage.

For discriminating and counting erythroblasts in body fluid samples by flow cytometry in accordance with the present invention, at least one fluorescent dye is employed, from the following selected group:

[Chem. 1]

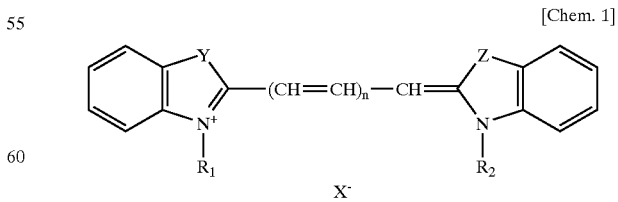

wherein $R_1$, $R_2$ are either a hydrogen molecule, an alkyl group, an alkynyl group or an alkyl group substituted with a hydroxyl, Y, Z are either sulfur, oxygen, nitrogen or carbon having a lower alkyl group, n is 0, 1 or 2, and $X^-$ is an anion;

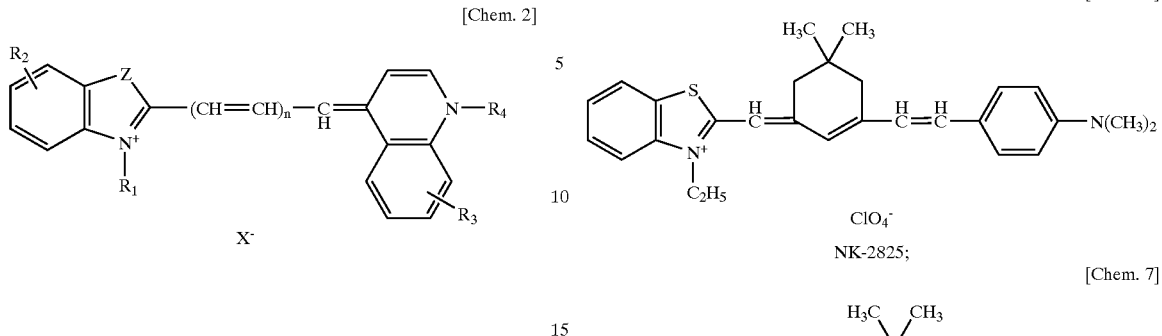

wherein $R_1$ is a hydrogen molecule or an alkyl group, $R_2$ and $R_3$ are a hydrogen molecule, a lower alkyl group or a lower alkoxy group. $R_4$ is a hydrogen molecule, an acyl group or an alkyl group, Z is sulfur, oxygen or carbon having a lower alkyl group, n is 0, 1 or 2, and $X^-$ is an anion;

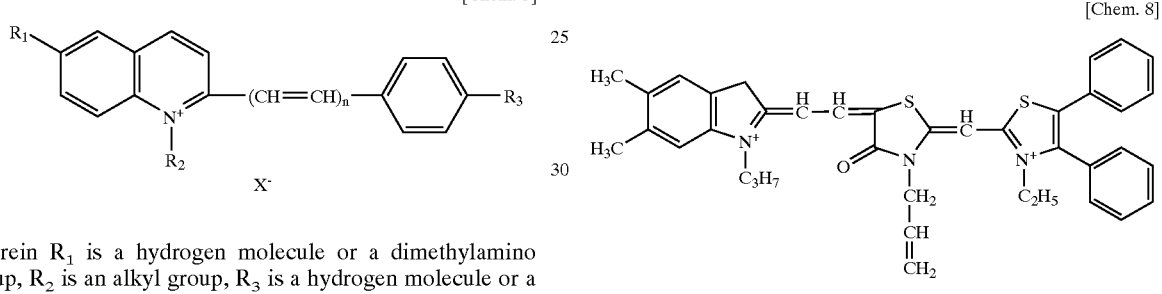

wherein $R_1$ is a hydrogen molecule or a dimethylamino group, $R_2$ is an alkyl group, $R_3$ is a hydrogen molecule or a dimethylamino group, n is 1 or 2, and $X^-$ is an anion;

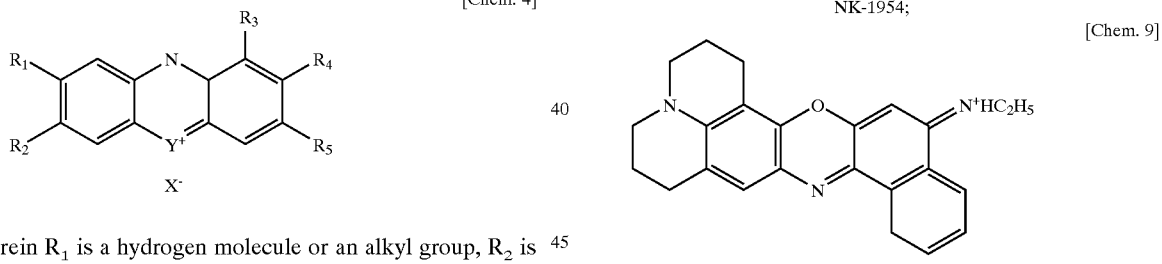

wherein $R_1$ is a hydrogen molecule or an alkyl group, $R_2$ is a dimethylamino group, $R_3$ is a hydrogen molecule or an amino group, $R_4$ is a hydrogen molecule, an alkyl group or an amino group, $R_5$ is a hydrogen molecule or a dimethylamino group, $X^-$ is an anion, and Y is sulfur or oxygen;

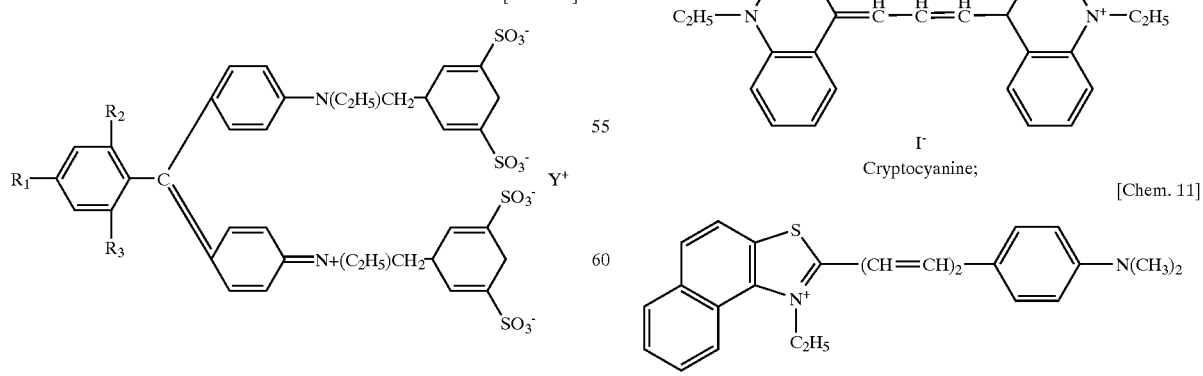

wherein $R_1$ is a hydrogen molecule or a hydroxyl, $R_2$, $R_3$ are a hydrogen molecule or a sulfonic group, and $Y^+$ is an alkali metal ion;

-continued

[Chem. 12]

NK-382;

[Chem. 13]

NK-2711;

[Chem. 14]

NK-138;

[Chem. 15]

Oxazine 720;

[Chem. 16]

LDS730;

[Chem. 17]

LD700;

-continued

[Chem. 18]

Nile Blue A;

[Chem. 19]

Brilliant Green;

[Chem. 20]

Iodine Green; and

[Chem. 21]

Malachite Green.

In general in the foregoing formulae, examples of an alkyl group bound to a nitrogen atom in a hetero-ring or a carbon atom that can be given are: alkyl groups having 1–20 carbons, preferably 1–10 carbons, or more preferably 1–6 carbons; for instance, methyl, ethyl, propyl, butyl, pentyl and hexyl. The lower alkyl groups or lower alkoxy groups are straight-chain or branched alkyl or alkoxy groups of 1–8 carbons, and preferably are methyl, ethyl, methoxy, or ethoxy. As acyl groups those of 1–3 carbons are preferable; for example, formyl, acetyl or propionyl. Preferable anions include halogens such as $F^-$ $Cl^-$, $Br^-$ as well as $I^-$, and $CF_3SO_3^-$, $BF_4^-$ and $ClO_4^-$.

Among the dyes recited in the foregoing, the NK series are from Nippon Kandoh Shikiso Kenkyusho Co., Ltd., and LDS730 and LD700 are from Exciton Inc.; the others are products that can be purchased commercially.

The selected fluorescent dye may be dissolved in the hemolytic agent, and made to act on the body fluid sample simultaneously with the hemolytic agent (and can be mixed with the hemolytic agent), or it may be added to the sample after a dissolving process (step thereof) in a proper solvent (water, lower alcohol, ethylene glycol, DMSO, etc.)

Although the concentration of the fluorescent dye differs depending on the dye used, it is generally in the range of 0.01 to 100 mg/l, preferably 0.1 to 10 mg/l and more preferably 0.3 to 3.0 mg/l These concentrations are for the state in which the dye solution is mixed with the hemolytic agent.

Wherein blood cells in the sample treated with the foregoing hemolytic agent were stained with the above-mentioned dye, leukocytes stained strongly and emitted an intense fluorescence when measured by the flow cytometer. On the other hand, erythroblasts stained weakly and emitted a faint fluorescence. The mechanism acting to give rise to the difference in fluorescence intensity between leukocytes and erythroblasts is not clear, however, it is thought that the taking up of the dye into the erythroblast nucleus is inhibited because the nucleus (DNA) is condensed.

As surfactants enabling discrimination and counting of erythroblasts into each of the erythroblast maturation stages, at least one kind among the surfactants from the group below is used.

[Chem. 22]

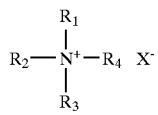

wherein $R_1$, $R_2$ and $R_3$ either identically or differently are hydrogen atoms, $C_{1-8}$ alkyl groups or $C_{6-8}$ aralkyl groups, $R_4$ is a $C_{8-18}$ alkyl group, $C_{8-18}$ alkenyl group, or a $C_{6-18}$ aralkyl group, and X- is an anion;

[Chem. 23]

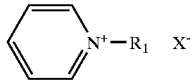

wherein $R_1$ is a $C_{8-18}$ alkyl group, and X- is an anion;

[Chem. 24]

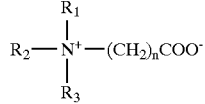

wherein $R_1$, $R_2$ either identically or differently are hydrogen atoms, $C_{1-8}$ alkyl groups or $C_{6-8}$ aralkyl groups, $R_3$ is a $C_{8-18}$ alkyl group, $C_{8-18}$ alkenyl group, or a $C_{6-18}$ aralkyl group, and n is 1 or 2;

[Chem. 25]

$$R_1-R_2-(CH_2CH_2O)_n-H$$

wherein $R_1$ is a $C_{9-25}$ alkyl group, alkenyl group or alkynyl group, $R_2$ is —O—,

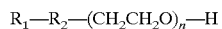

or —COO—, and n is 10 to 40;

[Chem. 26]

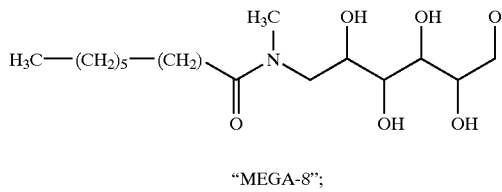

"MEGA-8";

[Chem. 27]

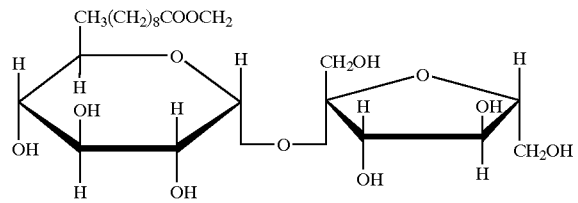

sucrose monocaprate;

[Chem. 28]

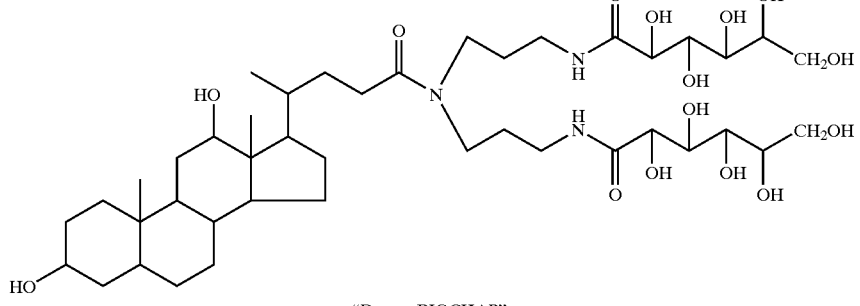

"Deoxy-BIGCHAP";

[Chem. 29]

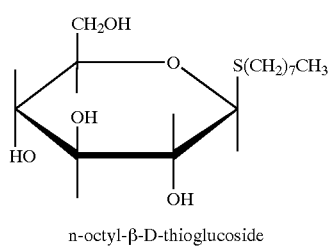

n-octyl-β-D-thioglucoside

-continued

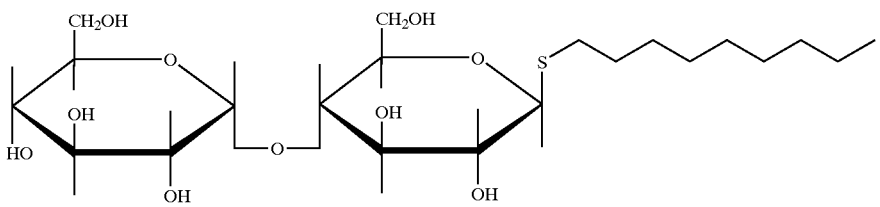
n-nonyl-β-D-thiomaltoside; [Chem. 30]

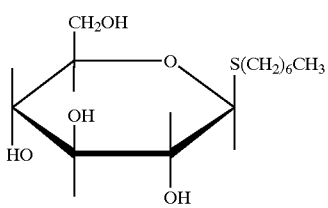
n-heptyl-β-D-thioglucoside; [Chem. 31]

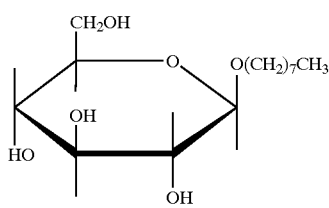
n-octyl-β-D-thioglucoside; [Chem. 32]

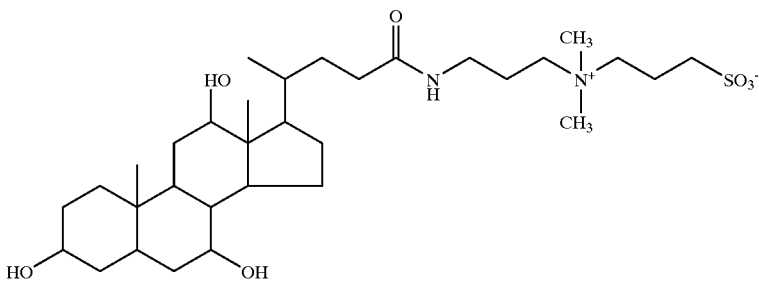
"CHAPS"; and [Chem. 33]

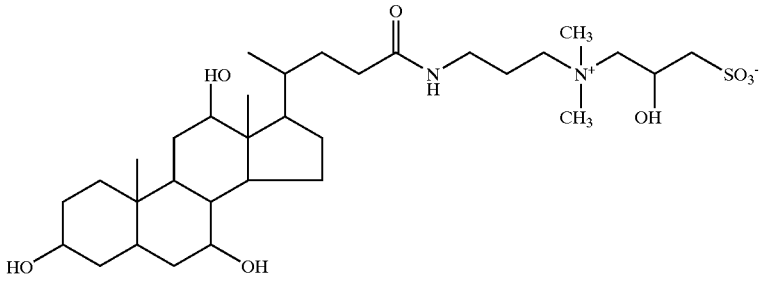
"CHAPSO." [Chem. 34]

In general in the foregoing formulae, octyl, heptyl, hexyl and benzyl can be cited as examples of $C_{1-8}$ alkyl groups or $C_{6-8}$ aralkyl groups. A $C_{1-3}$ alkyl group such as methyl or ethyl is preferable.

Octyl and benzyl can be given as examples of $C_{8-18}$ alkyl groups and $C_{8-18}$ alkenyl groups. $C_{10-18}$ straight-chain alkyl groups such as decyl, dodecyl and tetradecyl are preferable.

Decyl, dodecyl and tetradecyl can be given as examples of straight-chain $C_{8-18}$ alkyl groups. Nonyl, dodecyl, hexadecyl and oreyl can be given as examples of $C_{9-25}$ alkyl groups, alkenyl groups or alkynyl groups.

Among the above-recited surfactants, those listed from "MEGA-8" to CHAPSO" can be purchased from Dojindo Laboratories.

The concentration of surfactant is 10–10,000 mg/l, preferably 100–5000 mg/l, and more preferably 1000–3000 mg/l. These concentrations are of surfactant as contained in the hemolytic agent.

In a preferable mode of the present invention, a reagent of simple composition can be utilized, obtained by dissolving an organic acid such as salicylic acid, a dye, and a surfactant in purified water, and adjusting the pH using NaOH, HCl or the like. Samples are mixed with the reagent and reacted at 15–50° C., preferably 20–40° C. for a 3–120 second period, preferably a 5–40 second period.

The accordingly prepared assay sample is analyzed with the flow cytometer, measuring at least one scattered light parameter and at least one fluorescence parameter.

A scattered light parameter according to the present invention designates scattered light which can be measured by the general commercial flow cytometer, and can be low-angle forward scattered light (for example, wherein the received light angle is in the vicinity of 0–5 degrees) and a high-angle forward scattered light (for example, wherein the received light angle is in the vicinity of 5–20 degrees), or orthogonal/side scattered light. Preferably, a scattering angle that reflects leukocyte size information is chosen. Herein, low-angle forward scattered light is preferable.

Fluorescence as a parameter in the present invention is light emitted by dye bound to the above-described cell components, and a suitable received light wavelength is selected depending on the dye used. The fluorescent signal reflects the cytochemical characteristics of the cells.

The light source of the flow cytometer is not particularly limited; a light source of wavelength suitable to excite the dye is selected. For example, an argon-ion laser, a He—Ne laser or a red semiconductor laser can be used. The semiconductor laser is especially preferable, being quite inexpensive compared with gas lasers, making it possible to lower the costs of the device considerably.

Utilizing measured scattered light and difference in fluorescence intensity, erythroblasts are discriminated from the assay sample and counted; further erythroblasts are discriminated and counted by maturation stage. In the present invention, a process of utilizing measured scattered light an d difference in fluorescence intensity to discriminate erythroblasts from the assay sample and count the discriminated erythroblasts is a process of: (1) wherein the scattergram is for example drawn taking the X-axis for low-angle forward scattered light and the Y-axis for fluorescence, as shown for instance in FIG. 1, distributing the cells by forming them into erythroblast (NRBC), leukocyte (WBC) and hemoglobin-depleted erythrocyte (Ghost) populations (i.e., clusters); then (2) using suitable analyzing software, setting these populations into population regions, and by analyzing counts of cells contained within these regions, computing the number and proportion of erythroblasts. Further, in the present invention a process of discriminating and counting erythroblasts by maturation stage is a process of: (1) wherein the scattergram is for example drawn taking the X-axis for fluorescence and the Y-axis for low-angle forward scattered light, as shown for instance in FIG. 8, distributing the cells by forming them in populations (i.e., clusters) according to maturation stage; then (2) using suitable analyzing software, setting these populations into population regions, and by analyzing counts of cells contained within these regions, computing the number and proportion of erythroblast in the maturation stages.

The following examples will explain the present invention in further detail; however various modifications and alterations are possible, and the scope of the present invention is not limited to the embodiments below.

EXAMPLE 1

A reagent of the following composition was prepared.

| Ingredient | Quantity | Source |
| --- | --- | --- |
| salicylic acid | 10 mM | commercial product |
| NK-2825 | 0.3 mg/l | Nippon Kandoh Shikiso Kenkyusho Co., Ltd. |
| BC-20TX [polyoxyethylene (20) cetyl ether] | 3 g/l | Nikko Chemicals, Inc |
| purified water | 1 l | |

The pH was adjusted to 3.0 with NaOH. (Osmotic pressure: 30 mOsm/kg)

1.0 ml of the Example 1 reagent was added to 30 μl of anti-coagulant treated blood from a patient in whom erythroblasts had appeared in the peripheral circulation, and the preparation was reacted at 35° C. for 10 seconds. Subsequently fluorescence and low-angle forward scattered light were measured with a flow cytometer. The light source used was a 633 nm red semiconductor laser. The fluorescence measured was fluorescence of wavelength 660 nm or above.

Figure 2:
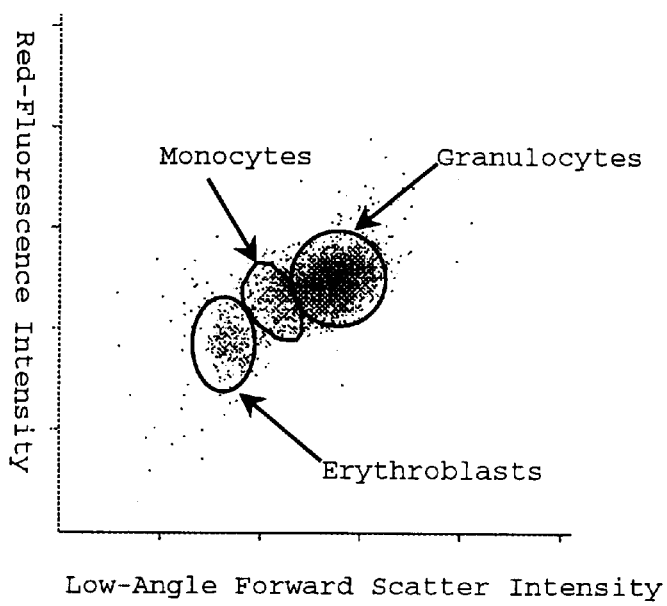
FIGS. 2–6 are red fluorescence intensity/low-angle forward scatter intensity scattergrams, each of a blood sample from a patient in whom erythroblasts had appeared in the peripheral circulation, and each assayed with the respective reagents of Examples 1–5.

FIG. 2 shows a scattergram in which the X-axis is taken for low-angle forward scattered light and the Y-axis for red fluorescence intensity. The blood cells form three populations: mononuclear leukocytes (lymphocytes, monocytes), granulocytes (neutrophils, eosinophils, basophils) and erythroblasts.

EXAMPLE 2

A reagent of the following composition was prepared.

| Ingredient | Quantity | Source |
| --- | --- | --- |
| salicylic acid | 10 mM | commercial product |
| NK-321 | 0.3 mg/l | Nippon Kandoh Shikiso Kenkyusho Co., Ltd. |
| BC-16 [polyoxyethylene (16) oleyl ether] | 3 g/l | Nikko Chemicals, Inc |
| purified water | 1 l | |

The pH was adjusted to 3.0 with NaOH. (Osmotic pressure: 32 mOsm/kg)

1.0 ml of the Example 2 reagent was added to 30 μl of anti-coagulant treated blood from a patient in whom erythroblasts had appeared in the peripheral circulation, and the preparation was reacted at 35° C. for 10 seconds. Subsequently fluorescence and low-angle forward scattered light were measured with a flow cytometer. The light source used was a 633 nm red semiconductor laser. The fluorescence measured was fluorescence of wavelength 660 nm or above.

Figure 3:
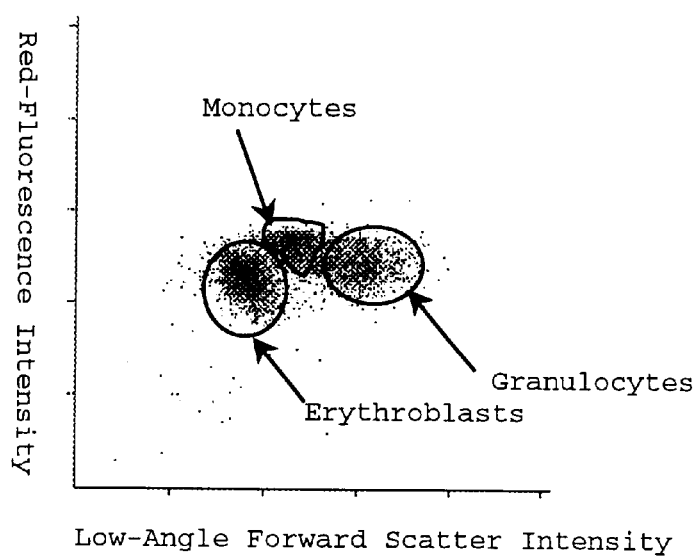

FIG. 3 shows a scattergram in which the X-axis is taken is for low-angle forward scattered light and the Y-axis for red fluorescence intensity. The blood cells form three populations: mononuclear leukocytes (lymphocytes, monocytes), granulocytes (neutrophils, eosinophils, basophils) and erythroblasts.

EXAMPLE 3

A reagent of the following composition was prepared.

| Ingredient | Quantity | Source |
| --- | --- | --- |
| salicylic acid | 10 mM | commercial product |
| NK-1836 | 3 mg/l | Nippon Kandoh Shikiso Kenkyusho Co., Ltd. |
| purified water | 1 l | |

The pH was adjusted to 3.0 with NaOH. (Osmotic pressure: 25 mOsm/kg)

1.0 ml of the Example 3 reagent was added to 30 μl of anti-coagulant treated blood from a patient in whom erythroblasts had appeared in the peripheral circulation, and the preparation was reacted at 35° C. for 10 seconds. Subsequently fluorescence and low-angle forward scattered light were measured with a flow cytometer. The light source used was a 633 nm red semiconductor laser. The fluorescence measured was fluorescence of wavelength 660 nm or above.

Figure 4:
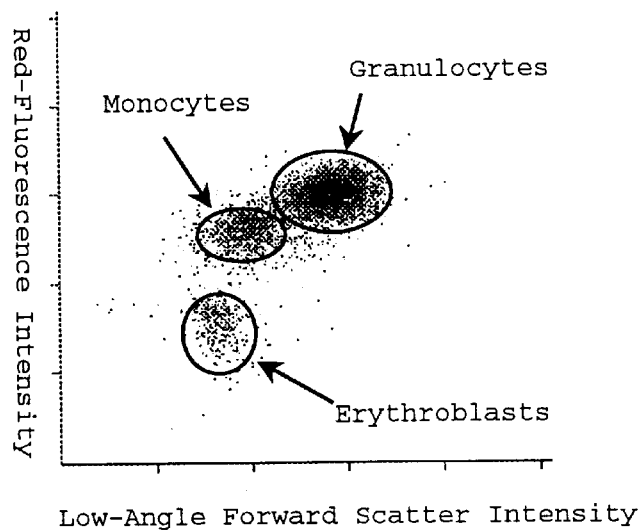

FIG. 4 shows a scattergram in which the X-axis is taken for low-angle forward scattered light and the Y-axis for red fluorescence intensity. The blood cells form three populations: mononuclear leukocytes (lymphocytes, monocytes), granulocytes (neutrophils, eosinophils, basophils) and erythroblasts.

EXAMPLE 4

A reagent of the following composition was prepared.

| Ingredient | Quantity | Source |
|---|---|---|
| salicylic acid | 10 mM | commercial product |
| DiIC1 (5) | 3 mg/l | Nippon Kandoh Shikiso Kenkyusho Co., Ltd. |
| purified water | 1 l | |

The pH was adjusted to 3.0 with NaOH. (Osmotic pressure: 25 mOsm/kg) 1.0 ml of the Example 4 reagent was added to 30 µl of anti-coagulant treated blood from a patient in whom erythroblasts had appeared in the peripheral circulation, and the preparation was reacted at 35° C. for 10 seconds. Subsequently fluorescence and low-angle forward scattered a light were measured with a flow cytometer. The light source used was a 633 nm red semiconductor laser. The fluorescence measured was fluorescence of wavelength 660 nm or above.

Figure 5:
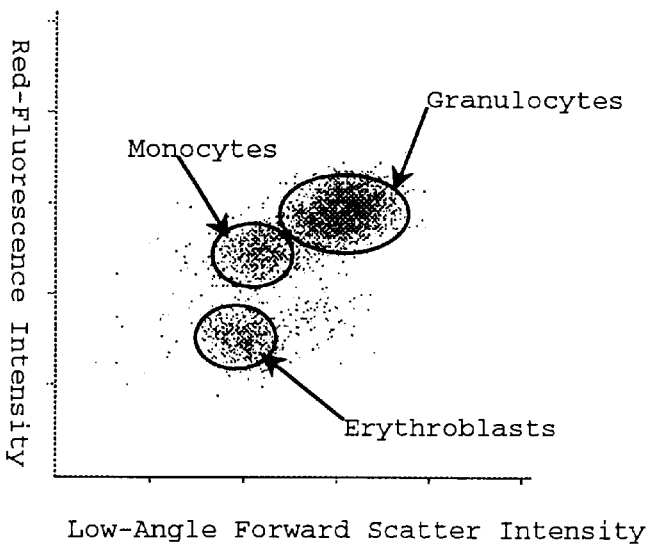

FIG. 5 shows a scattergram in which the X-axis is taken for low-angle forward scattered light and the Y-axis for red fluorescence intensity. The blood cells form three populations: mononuclear leukocytes (lymphocytes, monocytes), granulocytes (neutrophils, eosinophils, basophils) and erythroblasts.

EXAMPLE 5

A reagent of the following composition was prepared.

| Ingredient | Quantity | Source |
|---|---|---|
| salicylic acid | 10 mM | commercial product |
| Citric acid | 10 mM | commercial product |
| NK-1836 | 0.3 mg/l | Nippon Kandoh Shikiso Kenkyusho Co., Ltd. |
| purified water | 1 l | |

The pH was adjusted to 3.0 with NaOH. (Osmotic pressure: 40 mOsm/kg) 1.0 ml of the Example 5 reagent was added to 30 µl of anti-coagulant treated blood from a patient in whom erythroblasts had appeared in the peripheral circulation, and the preparation was reacted at 35° C. for 10 seconds. Subsequently fluorescence and low-angle forward scattered light were measured with a flow cytometer. The light source used was a 633 nm red semiconductor laser. The fluorescence measured was fluorescence of wavelength 660 nm or above.

Figure 6:
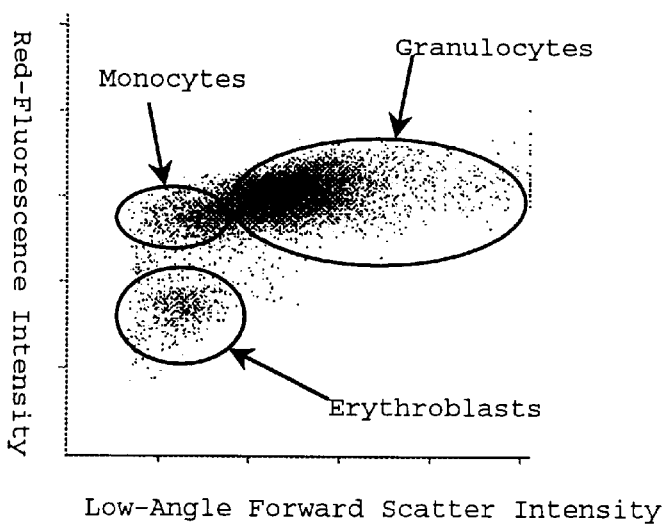

FIG. 6 shows a scattergram in which the X-axis is taken for low-angle forward scattered light and the Y-axis for red fluorescence intensity. The blood cells form three populations: mononuclear leukocytes (lymphocytes, monocytes), granulocytes (neutrophils, eosinophils, basophils) and erythroblasts.

In analyzing the cytometric plots produced in the foregoing embodiments and illustrated in the corresponding drawings, a window was established for each population and cell counts and the cell ratios were calculated within the windows.

Figure 7:
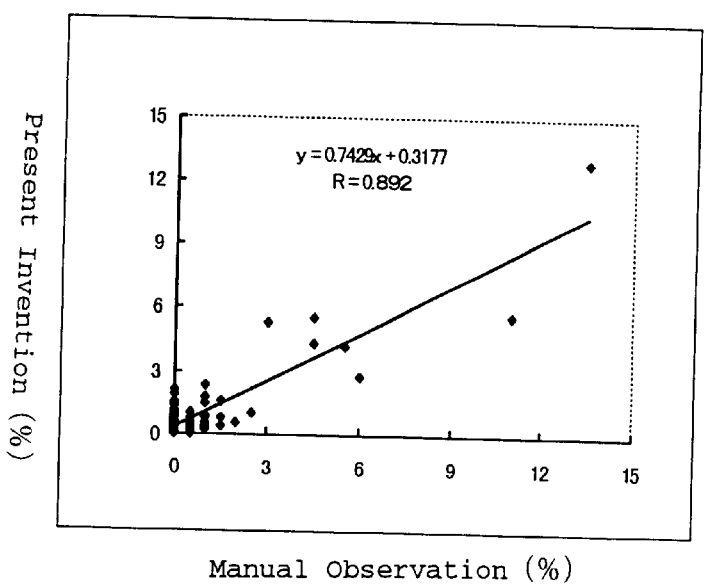
FIG. 7 is a diagram correlating results measured in accordance with the method of the present invention, with results obtained manually by microscopic observation.

FIG. 7 is a correlation diagram displaying the results wherein a manual method (May-Grunwald-Giemsa Stain, 500 count) and a method according to the present invention were utilized.

EXAMPLE 6

A reagent of the following composition was prepared.

| Ingredient | Quantity | Source |
|---|---|---|
| salicylic acid | 10 mM | commercial product |
| NK-2825 | 0.3 mg/l | Nippon Kandoh Shikiso Kenkyusho Co., Ltd. |
| LTAC [dodecyltrimethylammnonium chloride] | 0.3 g/l | Nikko Chemicals, Inc |
| purified water | 1 l | |

The pH was adjusted to 3.0 with NaOH. (Osmotic pressure: 40 mOsm/kg)

1.0 ml of the Example 6 reagent was added to 30 µl of anti-coagulant treated blood from a patient in whom erythroblasts had appeared in the peripheral circulation, and the preparation was reacted at 40° C. for 5 seconds. Subsequently fluorescence and low-angle forward scattered light were measured with a flow cytometer. The light source used was a 633 nm red semiconductor laser. The fluorescence measured was fluorescence of wavelength 660 nm or above.

Figure 8:
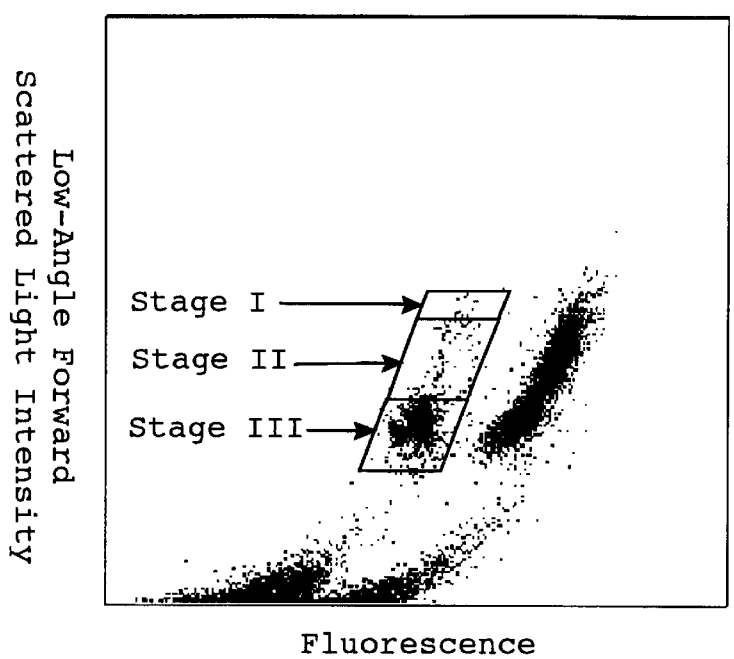
FIG. 8 is likewise a red fluorescence intensity/low-angle forward scatter intensity scattergram of a blood sample from a patient in whom erythroblasts had appeared in the peripheral circulation, assayed with the reagent of Example 6, demonstrating discrimination of erythroblasts into three maturation stage populations.

FIG. 8 shows a scattergram in which the X-axis is taken for red fluorescence intensity and the Y-axis for low-angle forward scattered light. The blood cells form four populations: leukocytes, Stage I erythroblasts, Stage II erythroblasts, and Stage III erythroblasts. (FIG. 9 diagrams the corresponding distribution. NRBC: nucleated red blood cells, WBC: white blood cells, and ghosts.)

After performing a May-Grünwald-Giemsa stain on the Example 6 blood sample, visual observation was carried out with a microscope. The erythroblasts were discriminated into proerythroblasts, basophilic erythroblasts, ploychromatophilic erythroblasts, and orthochromatophilic erythroblasts, and compared with the above-noted results obtained with the flow cytometer.

The table below shows the results from the flow cytometer and visual observation.

| Present Invention | | Visual Observation | |
|---|---|---|---|
| Stage I | 0.7% | proerythroblasts + basophlic erythroblasts | 0% |
| Stage II | 17.6% | polychromatophilic erythroblasts | 18% |
| Stage III | 81.7% | orthochromatophilic erythroblasts | 82.0% |

From the table above, it is evident that the results of the present invention and of visual observation agree well.

Figure 9:
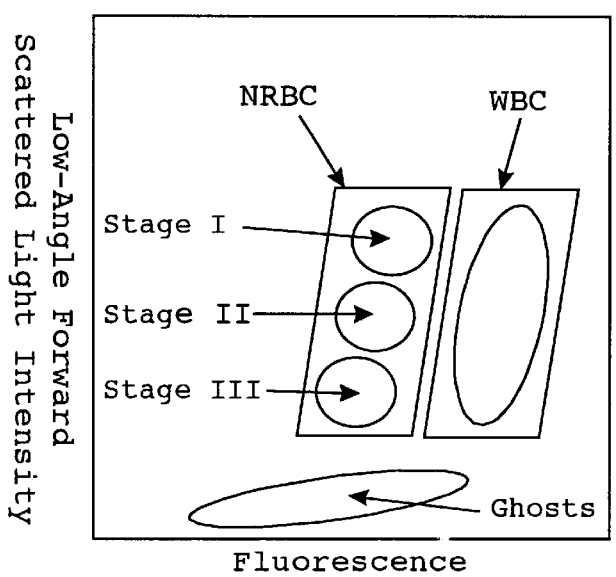
FIG. 9 is a drawing corresponding to FIG. 8, diagramming the blood cell populations discriminated from the sample with the Example 6 reagent.

In analyzing the cytometric plots produced in the in Example 6 and illustrated in FIGS. 8 and 9, a window was established for each population and cell counts and the cell ratios were calculated within the windows.

What is claimed is:

1. Reagents for discriminating and counting erythroblasts in body fluid samples by flow cytometry, consisting essentially of one fluorescent dye selected to stain leukocytes strongly and crythroblasts weakly in the body fluid samples to produce a flow-cytometric detectable intense fluorescence in the leukocytes relative to the erytlroblasts, the one fluo rescent dye being selected from the group consisting of the following:

wherein $R_1$, $R_2$ are either a hydrogen meolecule, an alkyl group, an alkynyl group or an alkyl group substituted with a hydroxyl, Y, Z are either sulfur, oxygen, nitrogen or carbon having a lower alkyl groups, n is 0, 1 or 2, and $X^-$ is an anion;

wherein $R_1$ is a hydrogen molecule or a dimethylamino group, $R_2$ is an alkyl group, $R_3$ is a hydrogen molecule or a dimethylamino group, n is 1 or 2, and $X^-$ is an anion;

wherein $R_1$ is a hydrogen molecule or an alkyl group, $R_2$ is a dimethylamino group, $R_3$ is a hydrogen molecule or an amino group, $R_4$ is a hydrogen molecule, an alkyl group or an amino group, $R_5$ is a hydrogen molecule or a dimethylamino group, $X^-$ is an anion, and Y is sulfur or oxygen;

wherein $R_1$ is a hydrogen molecule or a hydroxyl, $R_2$, $R_3$ are a hydrogen molecule or a sulfonic group, and $Y^+$ is an alkali metal ion;

NK-2825;

NK-1836;

NK-1954;

Oxazine 750;

Cryptocyanine;

NK-376;

NK-382;

NK-2711;

NK-138;

Oxazine 720;

-continued

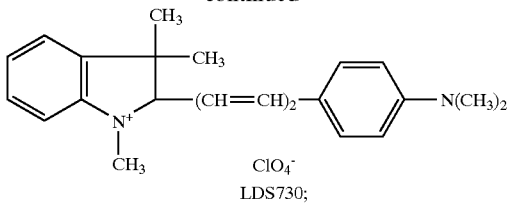
LDS730;

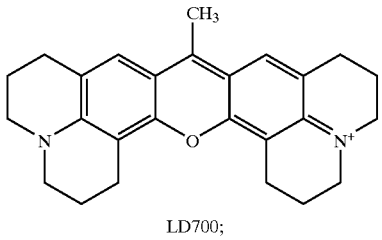
LD700;

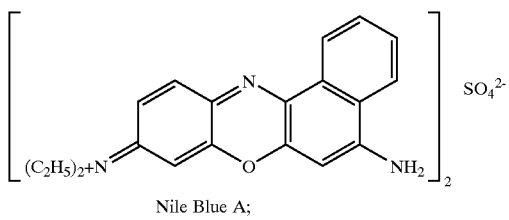
Nile Blue A;

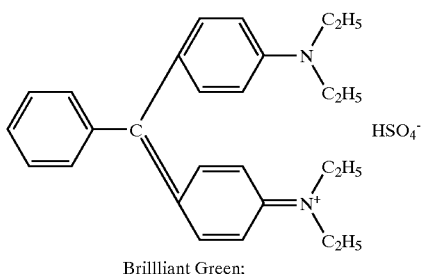
Brillliant Green;

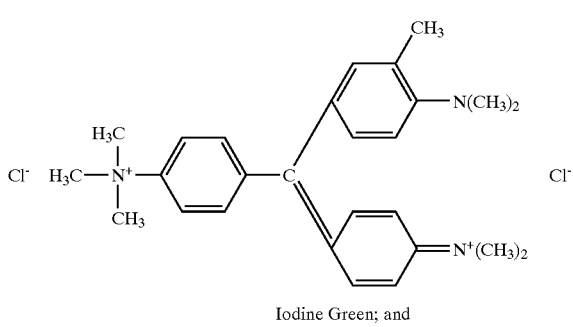
Iodine Green; and

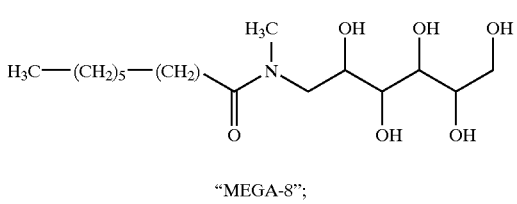
"MEGA-8";

-continued

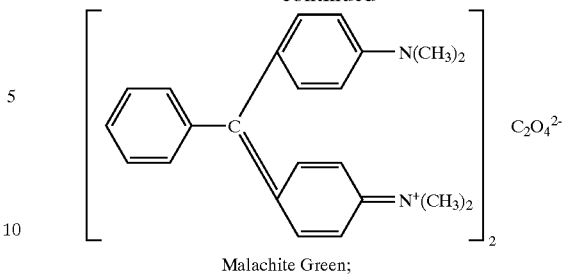
Malachite Green;

and a hemolytic agent containing intra-molecularly at least one of an organic acid having at least one aromatic ring, and a salt thereof, in an aqueous solution having a pH of approximately 2.0–5.0 and an osmotic pressure of approximately 100 mOsm/kg or less, for dissolving erythrocytes in a body fluid sample to an extent such that said hemolytic agent does not interfere with discrimination and counting by flow cytometry of erythroblasts in the body fluid sample, and such that said hemolytic agent conditions leukocytes and erythroblasts in the body fluid sample to be suitable for staining;

wherein said reagent has a pH of approximately 2.0 to 5.0.

2. Reagents as set forth in claim 1, wherein said organic acid is selected from salicylic acid, sodium salicylate and phthalic acid.

3. Reagents as set forth in claim 1, further including surfactant in a concentration of approximately 10 to 10,000 mg/l in the aqueous solution, the surfactant being selected from the group consisting of the following:

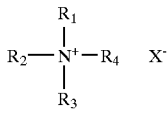

wherein $R_1$, $R_2$ and $R_3$ either identically or differently are hydrogen atoms, $C_{1-8}$ alkyl groups or $C_{6-8}$ aralkyl groups, $R_4$ is a $C_{8-18}$ alkyl group, $C_{8-18}$ alkenyl group, or a $C_{6-18}$ aralkyl group, and X– is an anion;

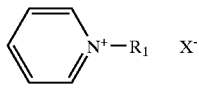

wherein $R_1$ is a $C_{8-18}$ alkyl group, and X– is an anion;

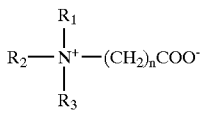

wherein $R_1$, $R_2$ either identically or differently are hydrogen atoms, $C_{1-8}$ alkyl groups or $C_{6-8}$ aralkyl groups, $R_3$ is a $C_{8-18}$ alkyl group, $C_{8-18}$ alkenyl group, or a $C_{6-18}$ aralkyl group, and n is 1 or 2;

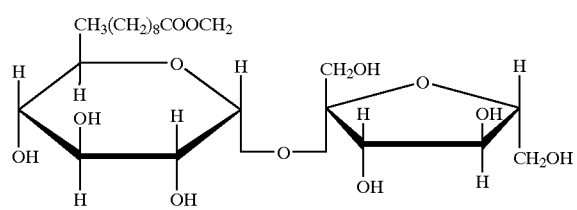
sucrose monocaprate;

-continued
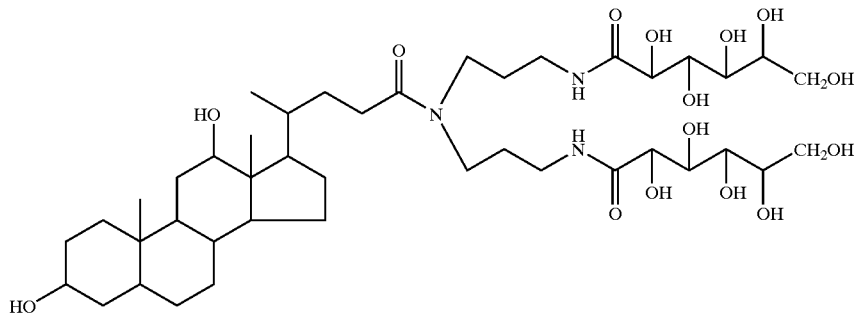
"Deoxy-BIGCHAP";
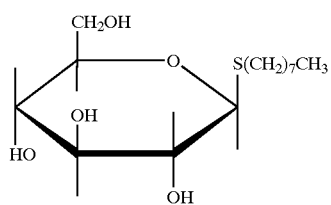
n-octyl-β-D-thioglucoside;
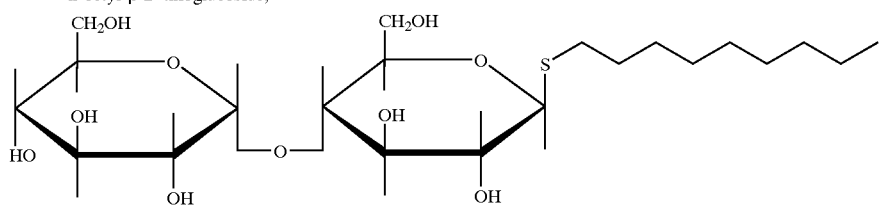
n-nonyl-β-D-thiomaltoside;
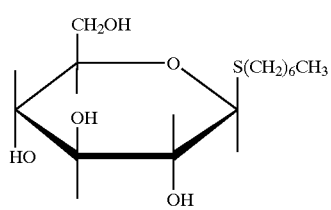
n-heptyl-β-D-thioglucoside;
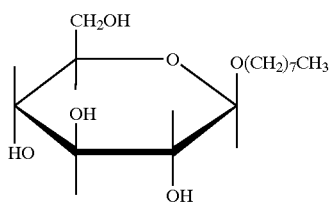
n-octyl-β-D-thioglucoside;
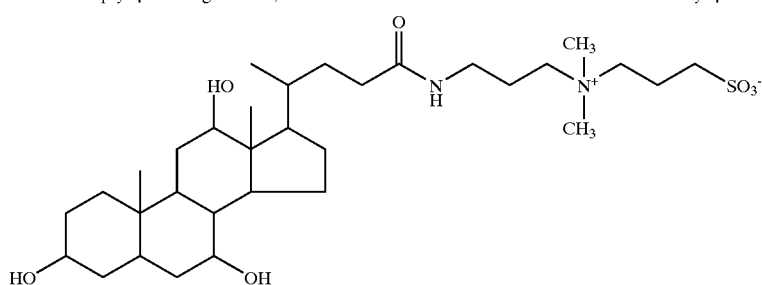
"CHAPS"; and
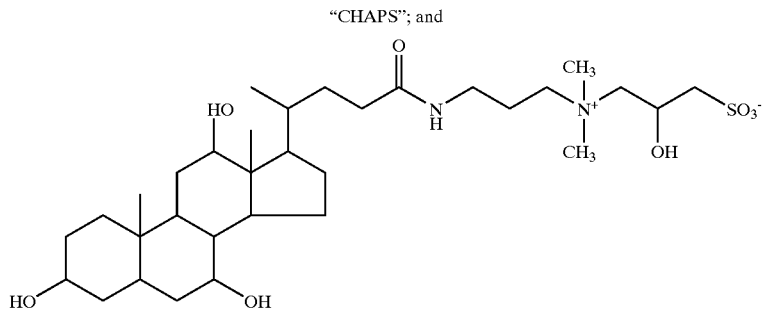
"CHAPSO."

wherein the surfactant enables flow cytometric discrimination and counting of erythroblasts in the body fluid samples by maturation stage.

4. Reagents as set forth in claim 1, wherein the body fluid samples are taken from one of the peripheral blood circulation, bone marrow and urine of a human patient.

5. A method for discriminating and counting erythroblasts from body fluid samples by flow cytometry, comprising the preparatory steps of:

(a) mixing a body fluid sample with a hemolytic agent containing intra-molecularly at least one of an organic acid having at least one aromatic ring and a salt thereof, in an aqueous solution having a pH of approximately 2.0–5.0 and an osmotic pressure of approximately 100 mOsm/kg or less, the hemolytic agent therein selected for dissolving erythrocytes within body fluid samples to an extent that does not interfere with flow-cytometric assaying, and for conditioning leukocytes and erythroblasts to be suitable for staining; and (b) staining leukocytes strongly and erythroblasts weakly in the body fluid samples to produce a flow-cytometric detectable intense fluorescence in the leukocytes relative to the erythroblasts by mixing the sample as prepared in said step (a) with one fluorescent dye selected from the group consisting of the following:

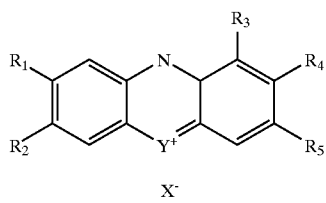

wherein $R_1$, $R_2$ are either a hydrogen molecule, an alkyl group, an alkynyl group or an alkyl group substituted with a hydroxyl, Y, Z are either sulfur, oxygen, nitrogen or carbon having lower alkyl groups, n is 0, 1 or 2, and $X^-$ is an anion;

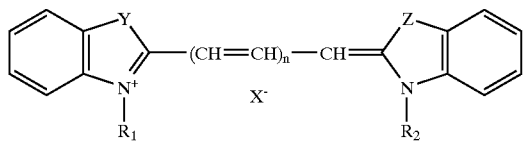

wherein $R_1$ is a hydrogen molecule or a dimethylamino group, $R_2$ is an alkyl group, $R_3$ is a hydrogen molecule or a dimethylamino group, n is 1 or 2, and $X^-$ is anion;

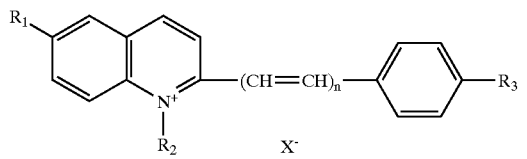

wherein $R_1$ is a hydrogen molecule or an alkyl group, $R_2$ is a dimethylamino group, $R_3$ is a hydrogen molecule or an amino group, $R_4$ is a hydrogen molecule, an alkyl group or an amino group, $R_5$ is a hydrogen molecule or a dimethylamino group, $X^-$ is an anion, and Y is either sulfur or oxygen;

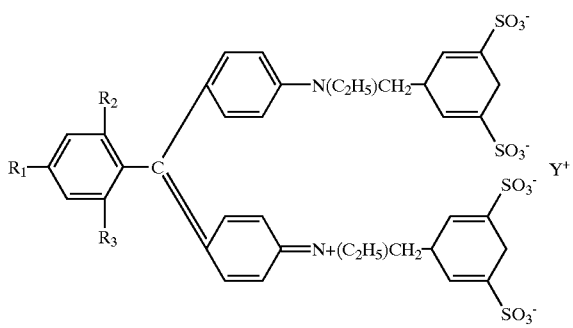

wherein $R_1$ is a hydrogen molecule or a hydroxyl, $R_2$, $R_3$ are a hydrogen molecule or a sulfonic group, and $Y^+$ is an alkali metal ion;

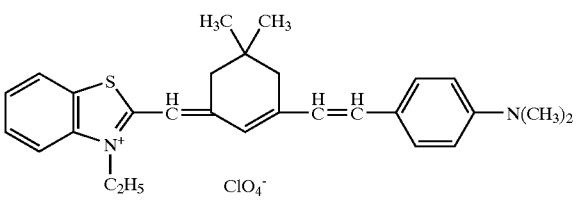

NK-2825;

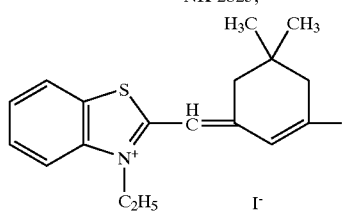

NK-1836;

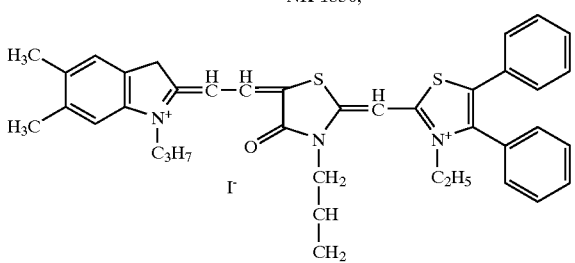

NK-1954;

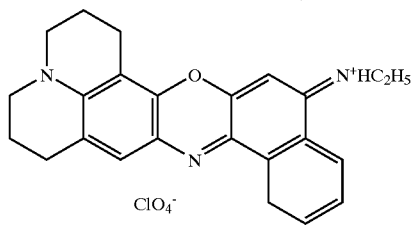

Oxazine 750;

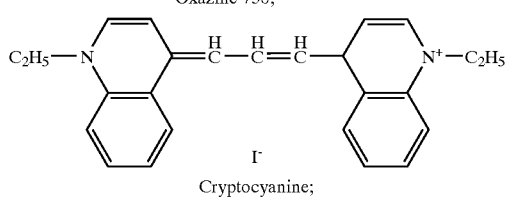

Cryptocyanine;

-continued

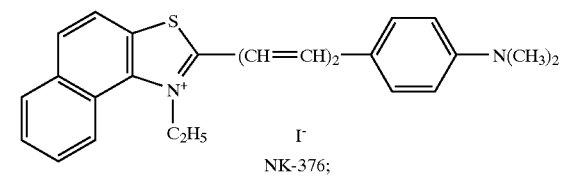
NK-376;

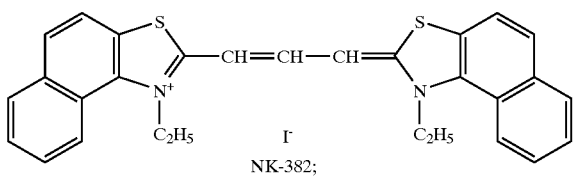
NK-382;

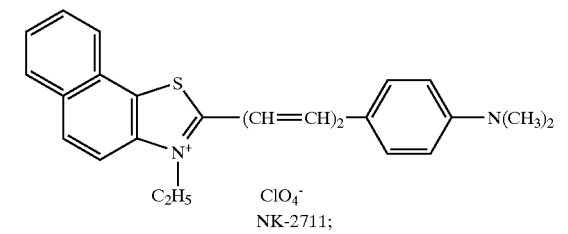
NK-2711;

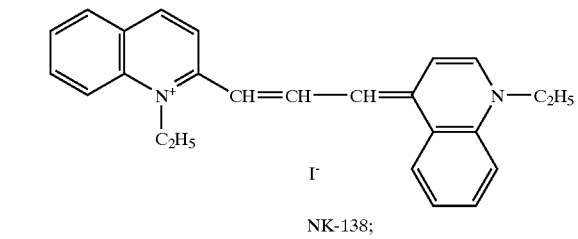
NK-138;

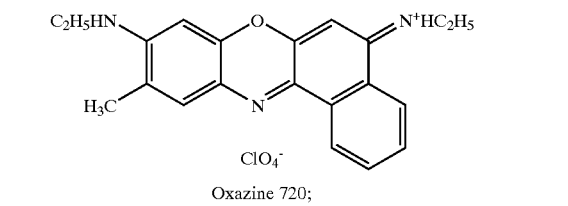
Oxazine 720;

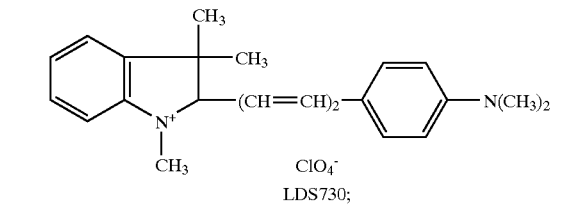
LDS730;

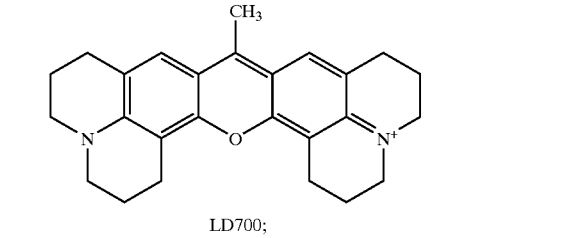
LD700;

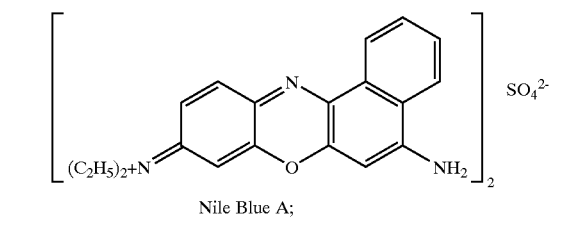
Nile Blue A;

-continued

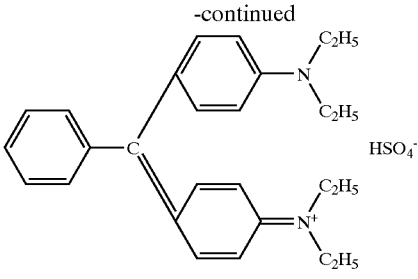
Brillliant Green;

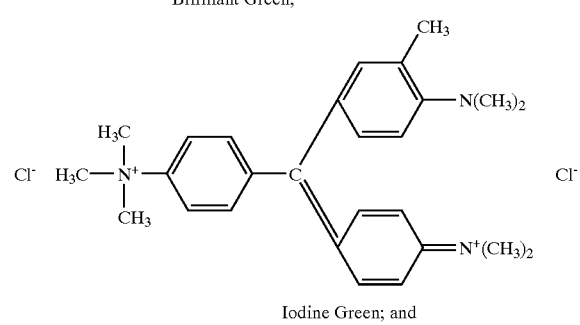
Iodine Green; and

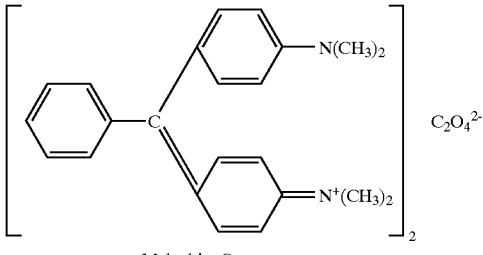
Malachite Green;

said hemolytic agent/dye mixture having a pH of approximately 2.0 to 5.0, said method further comprising the steps of:

(c) flow cytometrically assaying the sample as prepared in said step (b) by measuring at least one scattered light parameter and at least one fluorescence parameter; and (d) discriminating and counting erythroblasts utilizing intensity differences in scattered light and in fluorescence as measured in said step (c).

6. A method for discriminating and counting erythroblasts as set forth in claim 5, comprising the step of:

adding surfactant in a concentration of from approximately 10 to 10,000 mg/l to the hemolytic agent, wherein the surfactant is selected from the group consisting of the following:

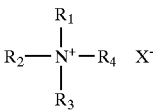

wherein $R_1$, $R_2$ and $R_3$ either identically or differently are hydrogen atoms, $C_{1-8}$ alkyl groups or $C_{6-8}$ aralkyl groups, $R_4$ is a $C_{8-18}$ alkyl group, $C_{8-18}$ alkenyl group, or a $C_{6-18}$ aralkyl group, X- is an anion;

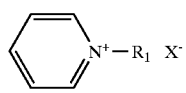

wherein $R_1$ is a $C_{8-18}$ alkyl group, and X– is an anion;

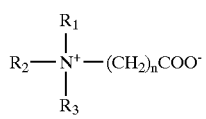

wherein $R_1$, $R_2$ either identically or differently are hydrogen atoms, $C_{1-8}$ alkyl groups or $C_{6-8}$ aralkyl groups, $R_3$ is a $C_{8-18}$ alkyl group, $C_{8-18}$ alkenyl group, or a $C_{6-18}$ aralkyl group, and n is the integer 1 or 2;

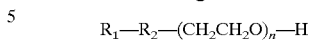

wherein $R_1$ is a $C_{9-25}$ alkyl group, alkenyl group or alkynyl group, $R_2$ is —O—,

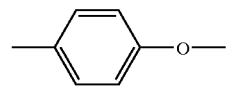

or —COO—, and n is 10 to 40;

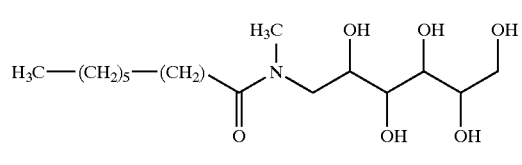

"MEGA-8";

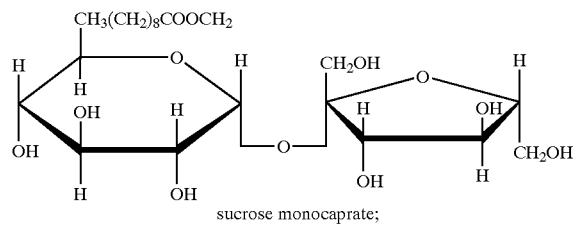

sucrose monocaprate;

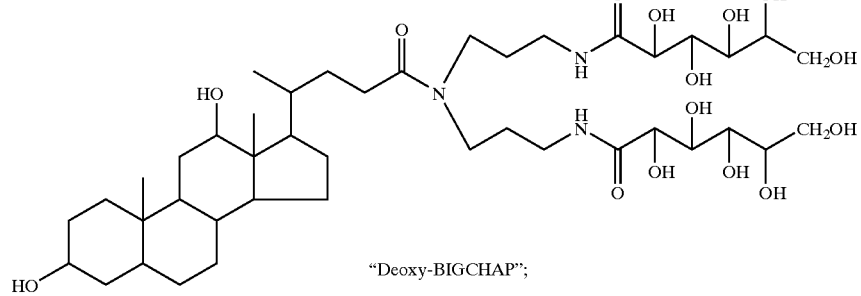

"Deoxy-BIGCHAP";

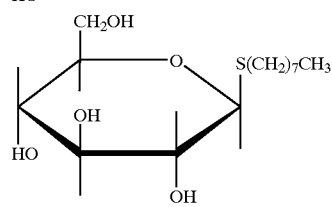

n-octyl-β-D-thioglucoside

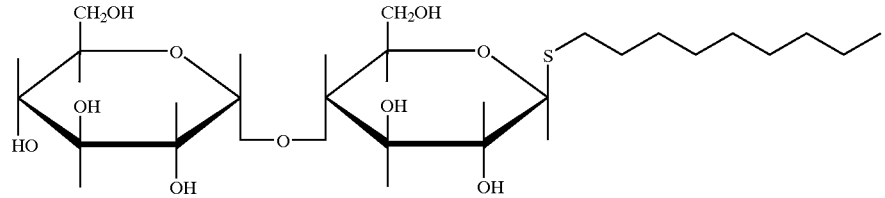

n-nonyl-β-D-thiomaltoside;

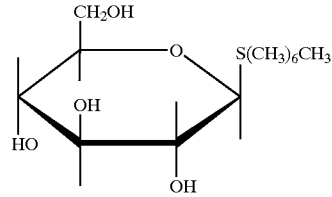

n-heptyl-β-D-thioglucoside;

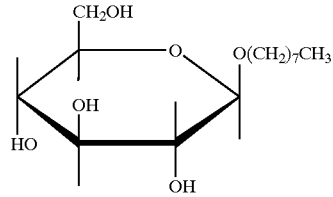

n-octyl-β-D-thioglucoside;

-continued

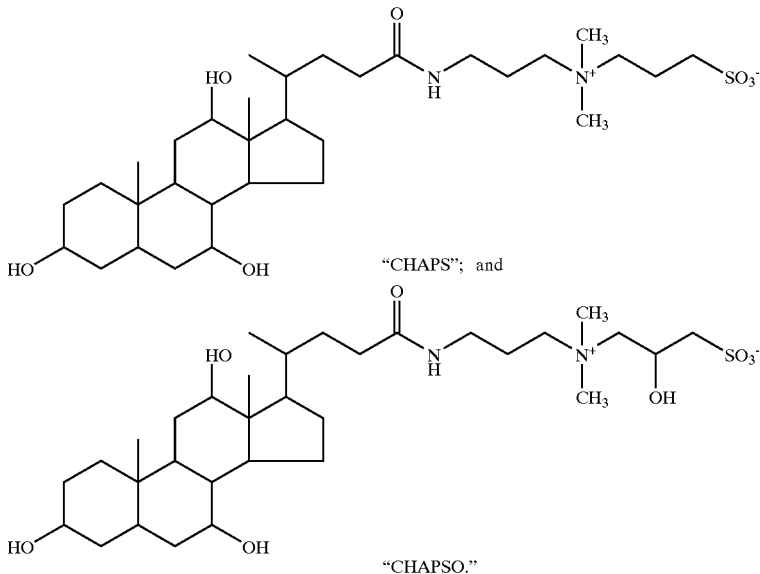

"CHAPS"; and "CHAPSO."

7. A method for discriminating and counting erythroblasts as set forth in claim 6, further comprising the step of flow cytometrically assaying the sample mixed with the hemolytic agent including the surfactant, by measuring the at least one scattered light parameter and at least one fluorescence parameter for discriminating and counting erythroblasts in the body fluid sample by maturation stage.

8. A method for discriminating and counting blasts as set forth in claim 5, wherein the scattered light parameter is at least one selected from low-angle forward scattered lights high-angle forward scattered light, and orthogonal scattered light as a selected angle of scattered light received in the flow cytometric assay.

9. A method for discriminating and counting erythroblasts as set forth in claim 7, wherein at least two erythroblast maturation stages are discriminated among erythroblasts in the body fluid sample.

10. A method for discriminating and counting erythroblasts as set forth in claim 5, wherein the body fluid samples are taken from one of the peripheral blood circulation, bone marrow and urine of a human patient.

11. Reagents for discriminating and counting erythroblasts in body fluid samples by flow cytometry, consisting essentially of one fluorescent dye selected to stain leukocytes strongly and erythroblasts weakly in the body fluid samples to produce a flow-cytometric detectable intense fluorescence in the leukocytes relative to the erythroblasts, the one fluorescent dye being selected from the group consisting of the following:

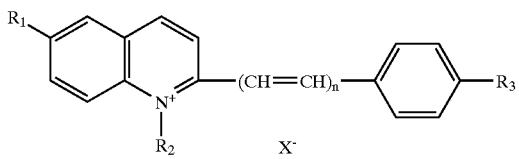

wherein $R_1$ is a hydrogen molecule or a dimethylamino group, $R_2$ is an alkyl group, $R_3$ is a hydrogen molecule or a dimethylamino group, n is 1 or 2, and $X^-$ is an anion;

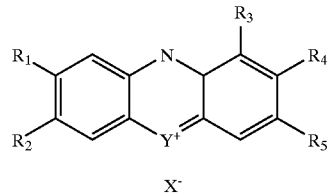

wherein $R_1$ is a hydrogen molecule or an alkyl group, $R_2$ is a dimethylamino group, $R_3$ is a hydrogen molecule or an amino group, $R_4$ is a hydrogen molecule, an alkyl group or an amino group, $R_5$ is a hydrogen molecule or a dimethylamino group, $X^-$ is an anion and Y is sulfur or oxygen;

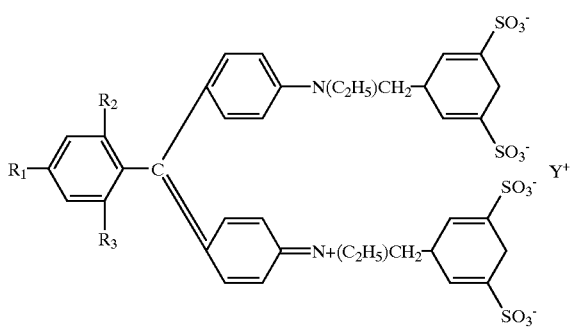

wherein $R_1$ is a hydrogen molecule or a hydroxyl, $R_2$, $R_3$ are a hydrogen molecule or a sulfonic group, and $Y^+$ is an alkali metal ion;

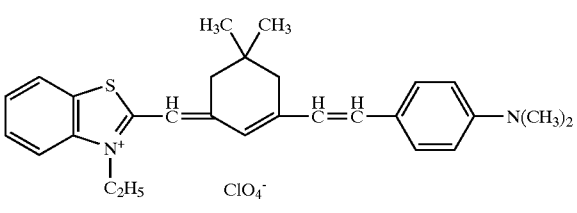

NK-2825;

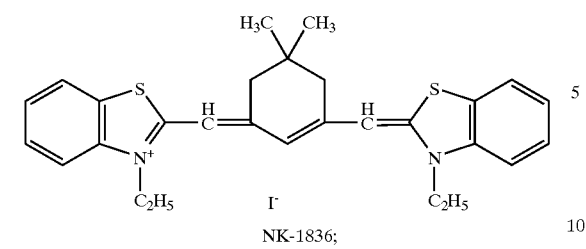
NK-1836;
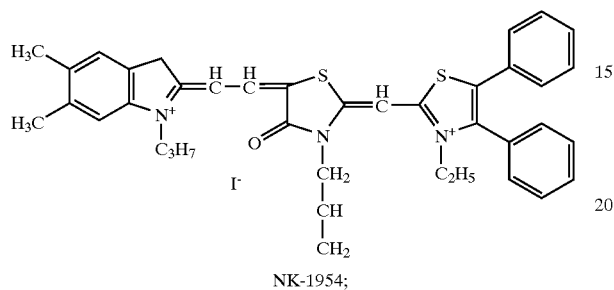
NK-1954;
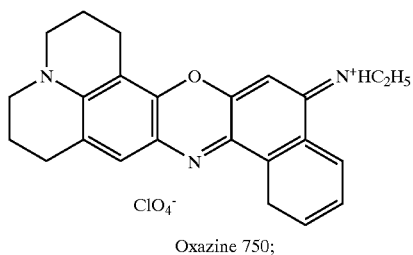
Oxazine 750;
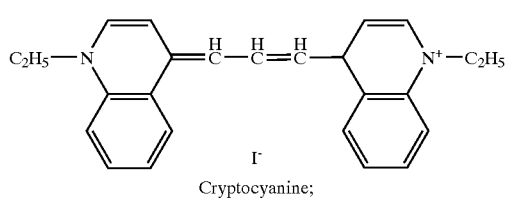
Cryptocyanine;
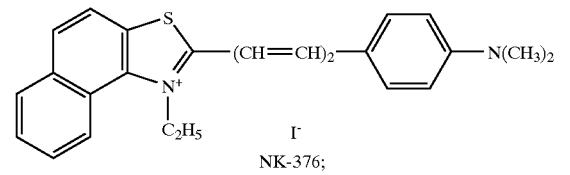
NK-376;
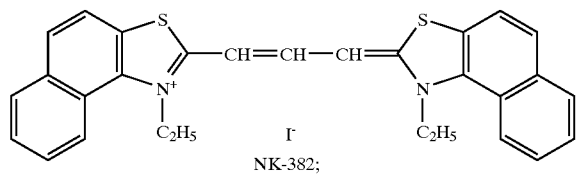
NK-382;
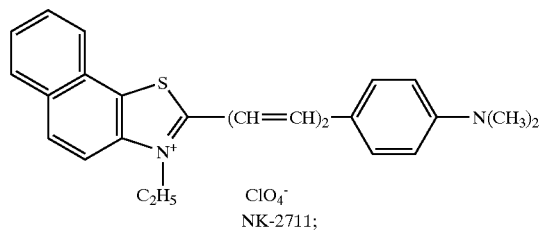
NK-2711;
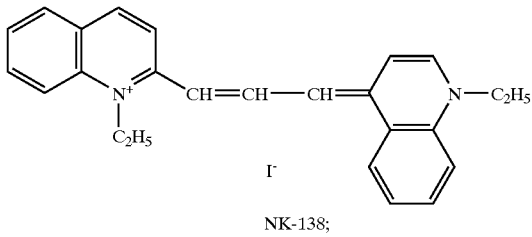
NK-138;
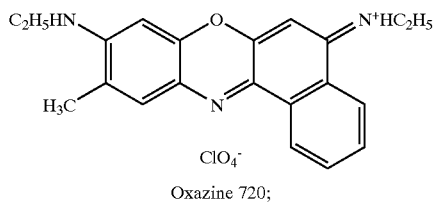
Oxazine 720;
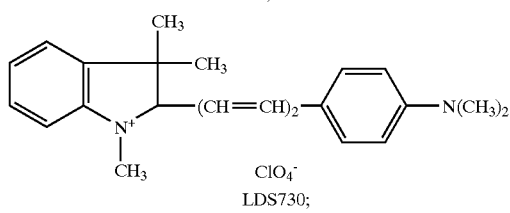
LDS730;
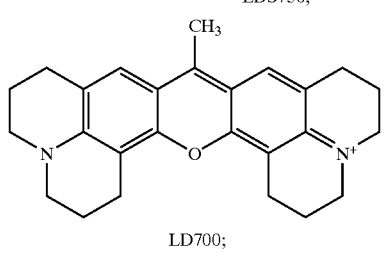
LD700;
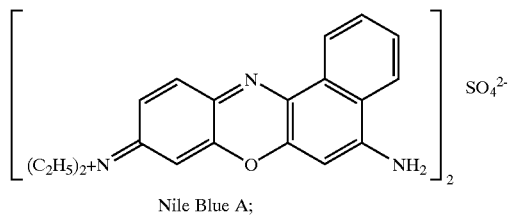
Nile Blue A;
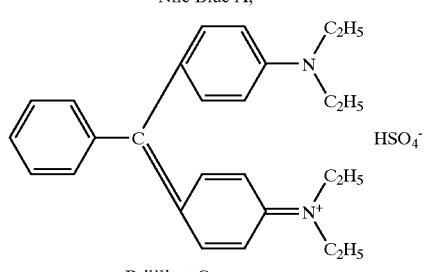
Brillliant Green;
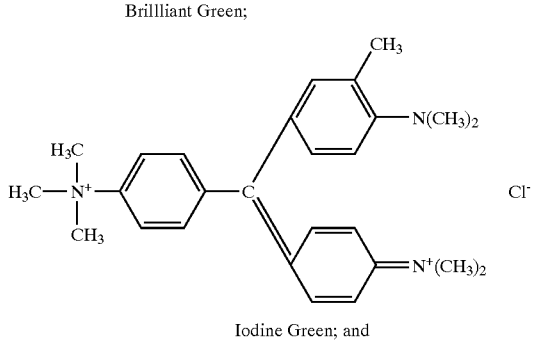
Iodine Green; and -continued

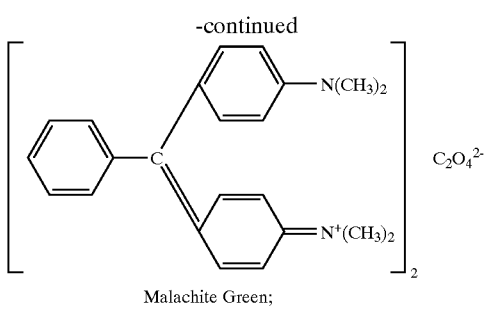

Malachite Green;

and a hemolytic agent in an aqueous solution having a pH of approximately 2.0–5.0 and an osmotic pressure of approximately 100 mOsm/kg or less for dissolving erythrocytes in a body fluid sample to an extent such that said hemolytic agent does not interfere with discrimination and counting by flow cytometry of erythroblasts in the body fluid sample, and such that said hemolytic agent conditions leukocytes and erythroblasts in the body fluid sample to be suitable for staining;

wherein said reagent has a pH of approximately 2.0 to 5.0.

12. Reagents as set fort in claim 11, wherein the hemolytic agent contains intramolecularly at least one of an organic acid having at least one aromatic ring, and a salt thereof.

13. Reagents as set forth in claim 12, wherein said organic acid is selected from salicylic acid, sodium salicylate and phthalic acid.

14. Reagents as set forth in claim 11, further including surfactant in a concentration of approximately 10 to 1 0,000 mg/l in the aqueous solution, the surfactant being selected from the group consisting of the following:

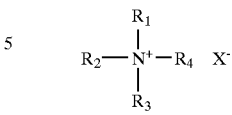

wherein $R_1$, $R_2$ and $R_3$ either identically or differently are hydrogen atoms, $C_{1-8}$ alkyl groups or $C_{6-8}$ aralkyl groups, $R_4$ is a $C_{8-18}$ alkyl group, $C_{8-18}$ alkenyl group, or a $C_{6-18}$ aralkyl group, and X– is an anion;

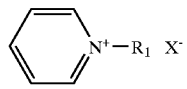

wherein $R_1$ is a $C_{8-18}$ alkyl group, and X– is an anion;

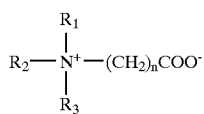

wherein $R_1$, $R_2$ either identically or differently are hydrogen atoms, $C_{1-8}$ alkyl groups or $C_{6-8}$ aralkyl groups, $R_3$ is a $C_{8-18}$ al group, $C_{8-18}$ alkenyl group, or a $C_{6-18}$ aralkyl group, and n is 1 or 2;

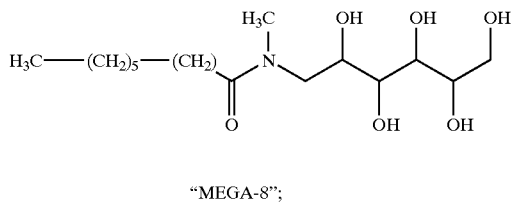

"MEGA-8";

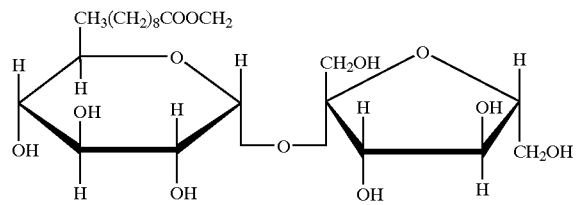

sucrose monocaprate;

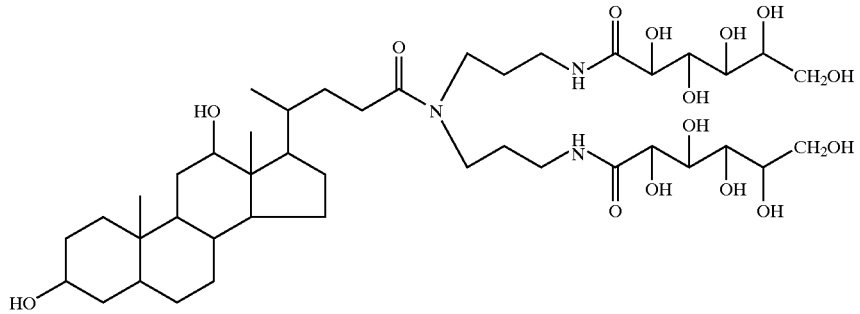

"Deoxy-BIGCHAP";

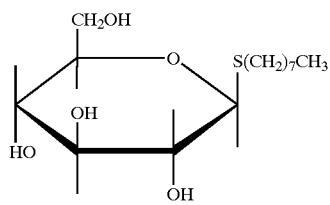

n-octyl-β-D-thioglucoside

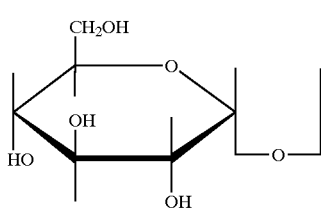

n-nonyl-β-D-thiomaltoside;

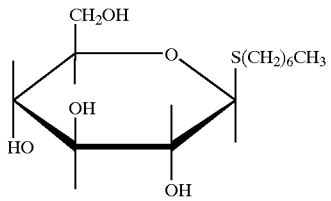

n-heptyl-β-D-thioglucoside;

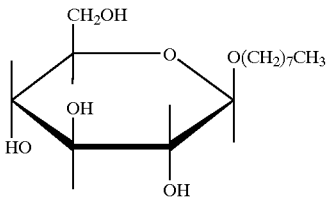

n-octyl-β-D-thioglucoside;

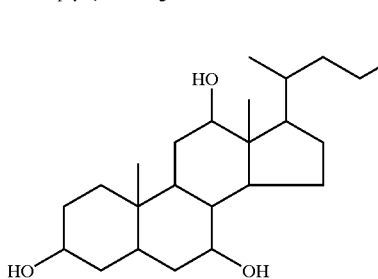

"CHAPS"; and

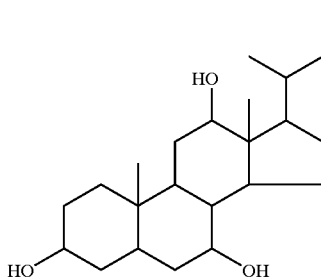

"CHAPSO";

wherein the surfactant enables flow cytometric discrimination and counting of erythroblasts in the body fluid samples by maturation stage.

15. Reagents as set forth in claim 11, wherein the body fluid samples are taken from one of the peripheral blood circulation, bone marrow and urine of a human patient.

16. Reagents for discriminating and counting erythroblasts in body fluid samples by flow cytometry, consisting essentially of one fluorescent dye selected to stain leukocytes strongly and erythroblasts weakly in the body fluid samples to produce a flow-cytometric detectable intense fluorescence in the leukocytes relative to the erythroblasts, the one fluorescent dye being selected from the group consisting of the following:

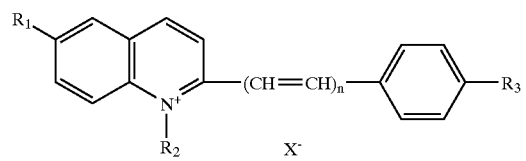

wherein $R_1$ is a hydrogen molecule or a dimethylamino group, $R_2$ is an alkyl group, $R_3$ is a hydrogen molecule or a dimethylamino group, n is 1 or 2, and $X^-$ is an anion;

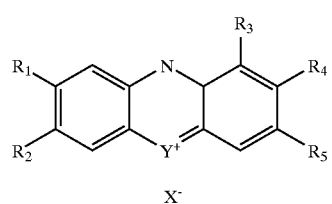

wherein $R_1$ is a hydrogen molecule or an alkyl group, $R_2$ is a dimethylamino group, $R_3$ is a hydrogen molecule or an amino group, $R_4$ is a hydrogen molecule, an alkyl group or an amino group, $R_5$ is a hydrogen molecule or a dimethylamino group, $X^-$ is an anion, and Y is sulfur or oxygen;

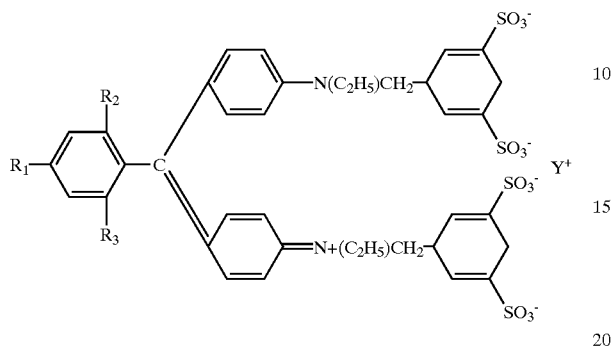

wherein $R_1$ is a hydrogen molecule or a hydroxyl, $R_2$, $R_3$ are a hydrogen molecule or a sulfonic group, and $Y^+$ is an alkali metal ion;

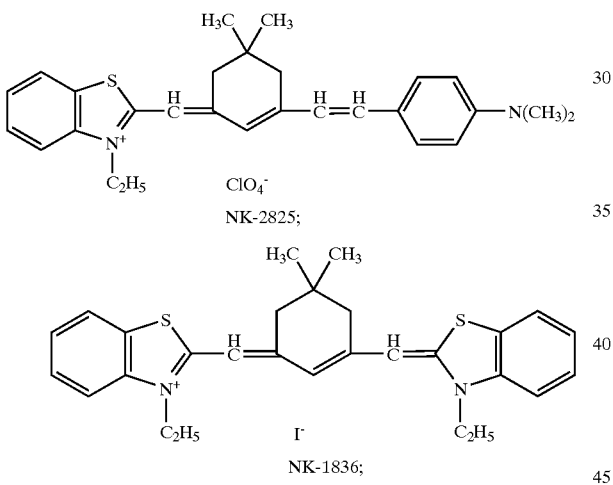

NK-2825;

NK-1836;

NK-1954;

Oxazine 750;

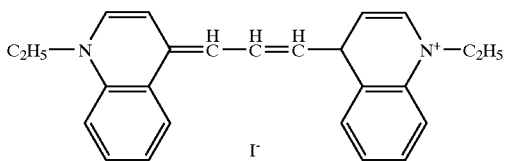

Cryptocyanine;

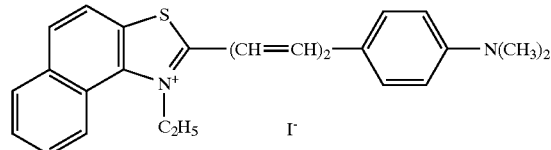

NK-376;

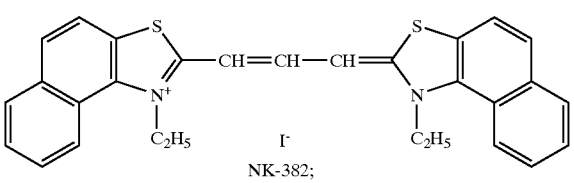

NK-382;

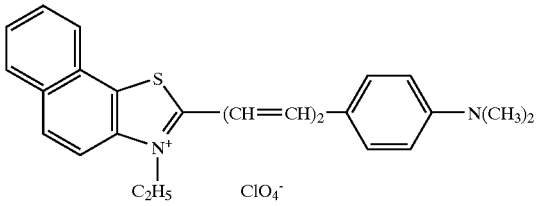

NK-2711;

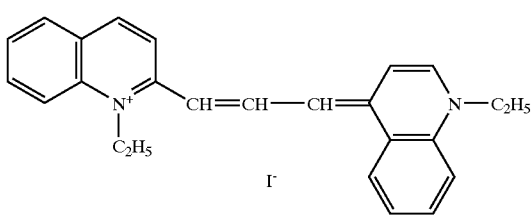

NK-138;

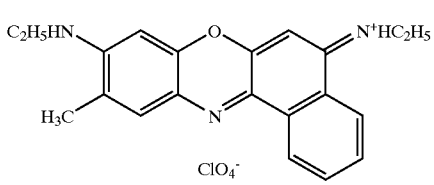

Oxazine 720;

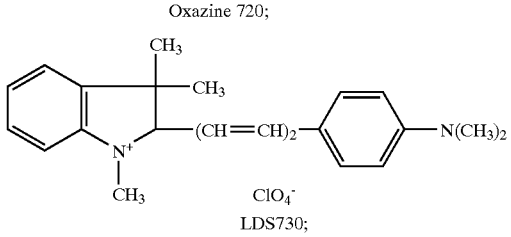

LDS730;

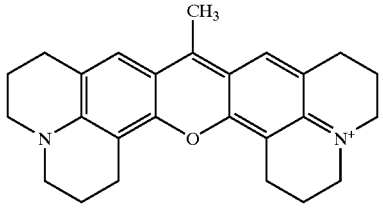

LD700;

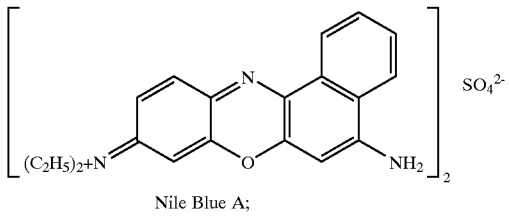

Nile Blue A;

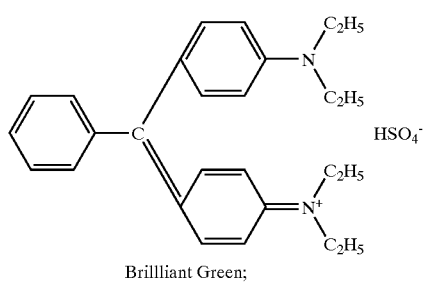

Brillliant Green;

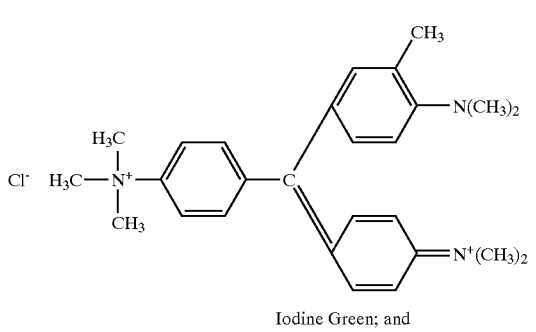

Iodine Green; and

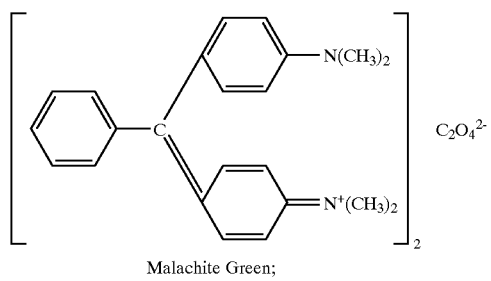

Malachite Green;

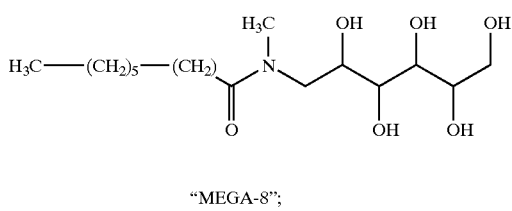

"MEGA-8";

and a hemolytic agent containing intra-molecularly at least one of an organic acid having at least one aromatic ring, and a salt thereof, in an aqueous solution having a pH of approximately 2.0–5.0 and an osmotic pressure of approximately 100 mOsm/kg or less, for dissolving erythrocytes in a body fluid sample to an extent such that said hemolytic agent does not interfere with discrimination and counting by flow cytometry of erythroblasts in the body fluid sample, and such that said hemolytic agent conditions leukocytes and erythroblasts in the body fluid sample to be suitable for staining;

wherein said reagent has a pH of approximately 2.0 to 5.0.

17. Reagents as set forth in claim 16, wherein said organic acid is selected from salicylic acid, sodium salicylate and phthalic acid.

18. Reagents as set forth in claim 16, further including surfactant in a concentration of approximately 10 to 10,000 mg/l in the aqueous solution, the surfactant being selected from the group consisting of the following:

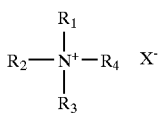

wherein $R_1$, $R_2$ and $R_3$ either identically or differently are hydrogen atoms, $C_{1-8}$ alkyl groups or $C_{6-8}$ aralkyl groups, $R_4$ is a $C_{8-18}$ alkyl group, $C_{8-18}$ alkenyl group, or a $C_{6-18}$ aralkyl group, and X– is an anion;

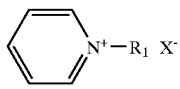

wherein $R_1$ is a $C_{8-18}$ alkyl group, and X– is an anion;

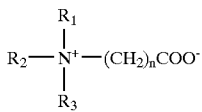

wherein $R_1$, $R_2$ either identically or differently are hydrogen atoms, $C_{1-8}$ alkyl groups or $C_{6-8}$ aralkyl groups, $R_3$ is a $C_{8-18}$ alkyl group, $C_{8-18}$ alkenyl group, or a $C_{6-18}$ aralkyl group, and n is 1 or 2;

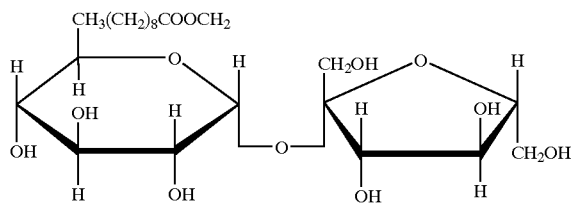

sucrose monocaprate;

-continued
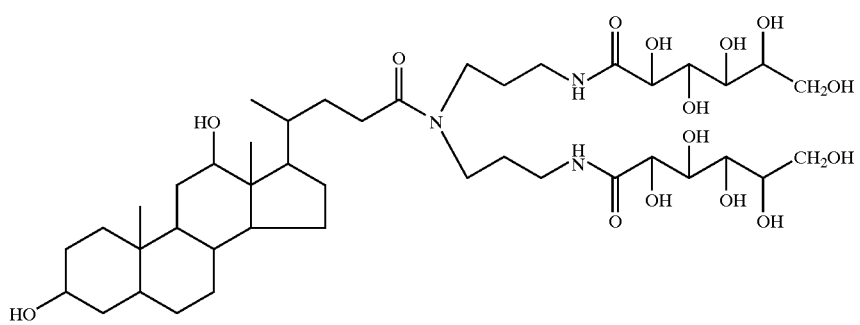
"Deoxy-BIGCHAP";
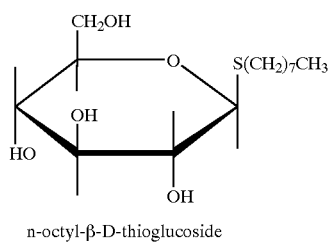
n-octyl-β-D-thioglucoside
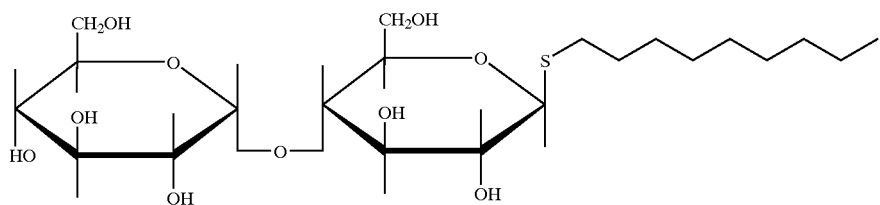
n-nonyl-β-D-thiomaltoside;
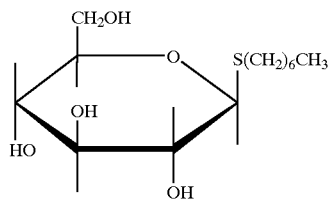
n-heptyl-β-D-thioglucoside;
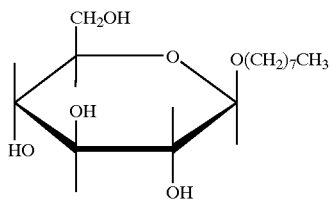
n-octyl-β-D-thioglucoside;
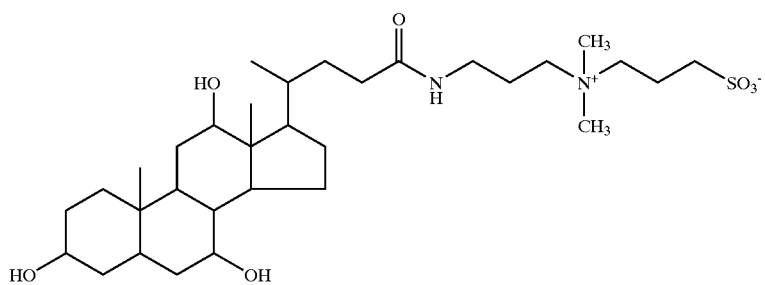
"CHAPS"; and -continued

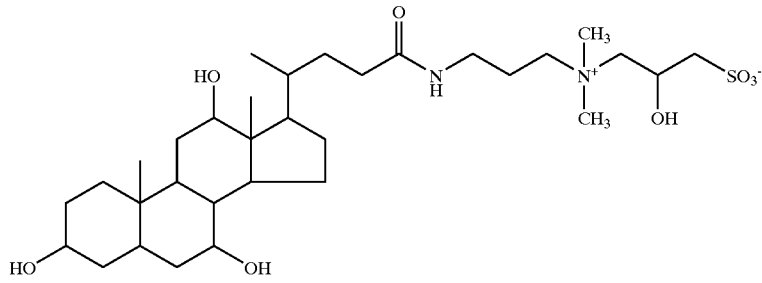

"CHAPSO";

wherein the surfactant enables flow cytometric discrimination and counting of erythroblasts in the body fluid samples by maturation stage.

19. Reagents as set forth in claim 16, wherein the body fluid samples are taken from one of the peripheral blood circulation, bone marrow and urine of a human patient.

20. A method for discriminating and counting erythroblasts from body fluid samples by flow cytometry, comprising the preparatory steps of:

(a) mixing a body fluid sample with a hemolytic agent containing intra-molecularly at least one of an organic acid having at least one aromatic ring, and a salt thereof, in an aqueous solution having a pH of approximately 2.0–5.0 and an osmotic pressure of approximately 100 mOsm/kg or less, the hemolytic agent therein selected for dissolving erythrocytes within body fluid samples to an extent that does not interfere with flow-cytometric assaying, and for conditioning leukocytes and erythroblasts to be suitable for staining; and (b) staining leukocytes strongly and erythroblasts weakly in the body fluid samples to produce a flow-cytometric detectable intense fluorescence in the leukocytes relative to the erythroblasts by mixing the sample as prepared in said step (a) with one fluorescent dye selected from the group consisting of the following:

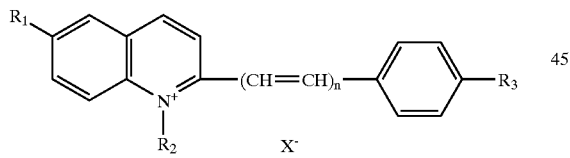

wherein $R_1$ is a hydrogen molecule or a dimethylamino group, $R_2$ is an alkyl group, $R_3$ is a hydrogen molecule or a dimethylamino group, n is 1 or 2, and $X^-$ is anion;

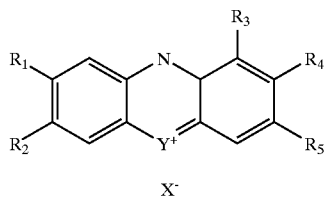

wherein $R_1$ is a hydrogen molecule or an alkyl group, $R_2$ is a dimethylamino group, $R_3$ is a hydrogen molecule or an amino group, $R_4$ is a hydrogen molecule, an alkyl group or an amino group, $R_5$ is a hydrogen molecule or a dimethylamino group, $X^-$ is an anion, and Y is either sulfur or oxygen;

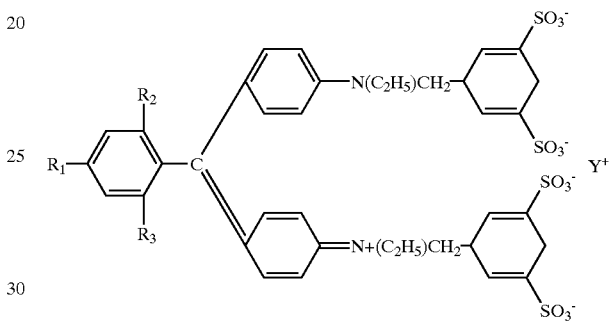

wherein $R_1$ is a hydrogen molecule or a hydroxyl, $R_2$, $R_3$ are a hydrogen molecule or a sulfonic group, and $Y^+$ is an alkali metal ion;

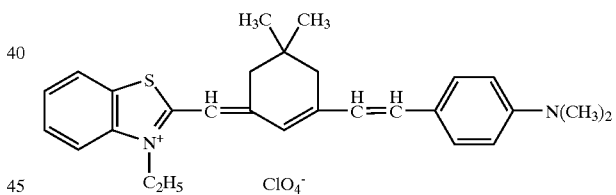

NK-2825;

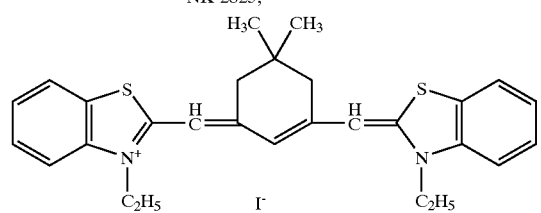

NK-1836;

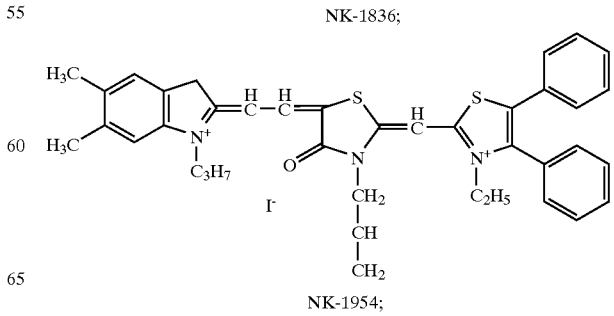

NK-1954;

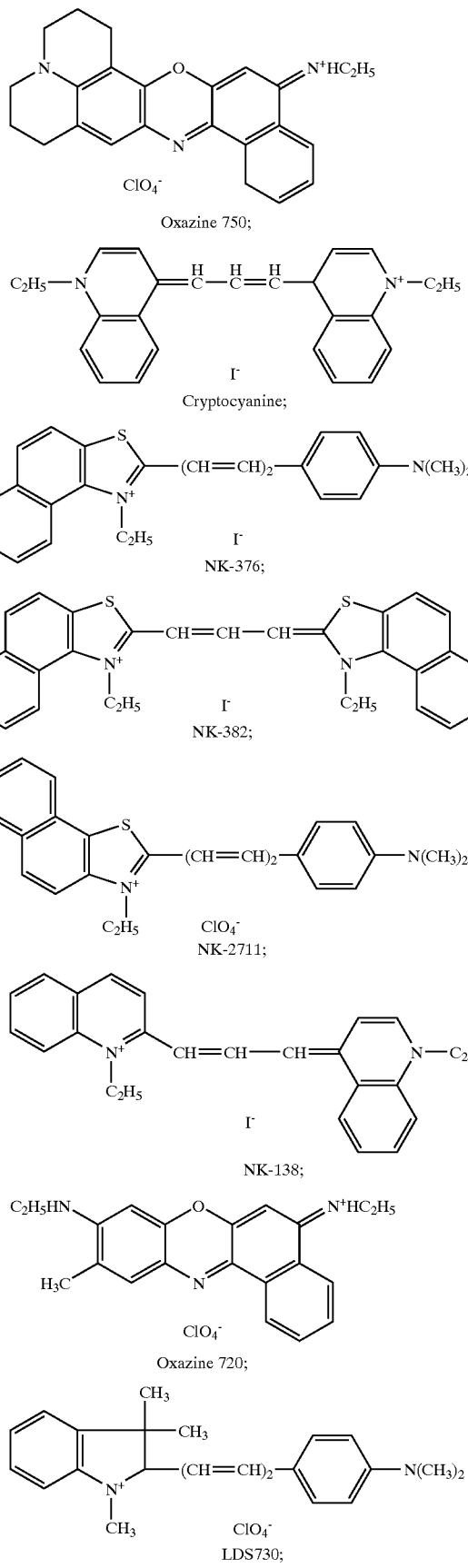

Oxazine 750;

Cryptocyanine;

NK-376;

NK-382;

NK-2711;

NK-138;

Oxazine 720;

LDS730;

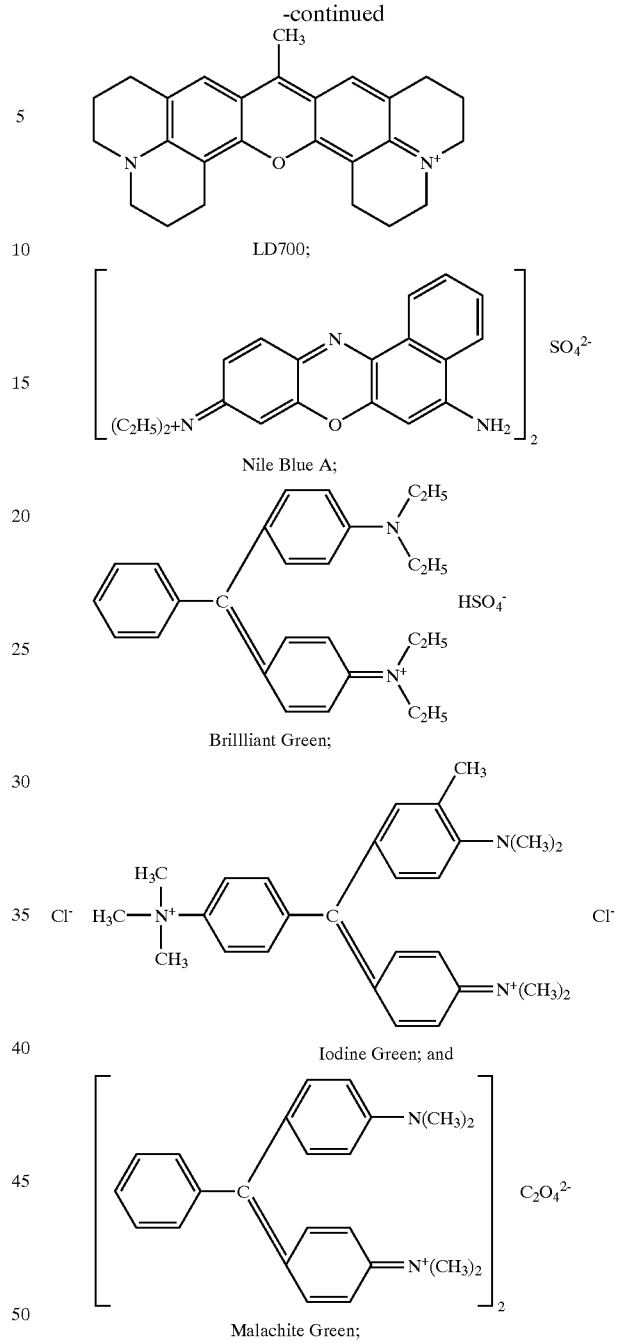

LD700;

Nile Blue A;

Brillliant Green;

Iodine Green; and

Malachite Green;

said haemolytic agent/dye mixture having a pH of approximately 2.0 to 5.0, said method further comprising the steps of:

(c) flow cytometrically assaying the sample as prepared in said step (b) by measuring at least one scattered light parameter and at least one fluorescence parameter; and (d) discriminating and counting erythroblasts utilizing intensity differences in scattered light and in fluorescence as measured in said step (c).

21. A method for discriminating and counting erythroblasts as set forth in claim 20, further comprising the step of:

adding surfactant in a concentration of from approximately 10 to 10,000 mg/l to the hemolytic agent,- wherein the surfactant is selected from the group consisting of the following:

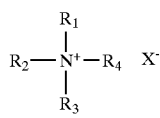

wherein $R_1$, $R_2$ and $R_3$ either identically or differently are hydrogen atoms, $C_{1-8}$ alkyl groups or $C_{6-8}$ aralkyl groups, $R_4$ is a $C_{8-18}$ alkyl group, $C_{8-18}$ alkenyl group, or a $C_{6-18}$ aralkyl group, and X− is an anion;

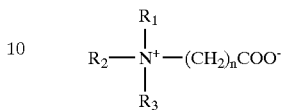

wherein $R_1$ is a $C_{8-18}$ alkyl group, and X− is an anion;

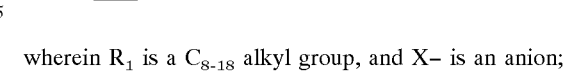

wherein $R_1$, $R_2$ either identically or differently are hydrogen atoms, $C_{1-8}$ alkyl groups or $C_{6-8}$ aralkyl groups, $R_3$ is a $C_{8-18}$ alkyl group, $C_{8-18}$ alkenyl group, or a $C_{6-18}$ aralkyl group, and n is the integer 1 or 2;

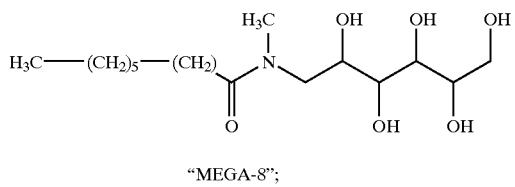

"MEGA-8";

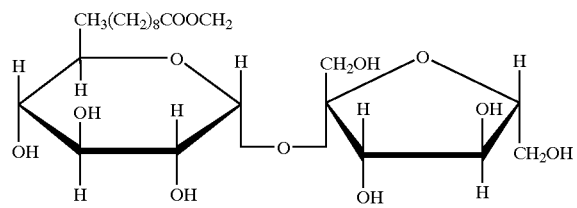

sucrose monocaprate;

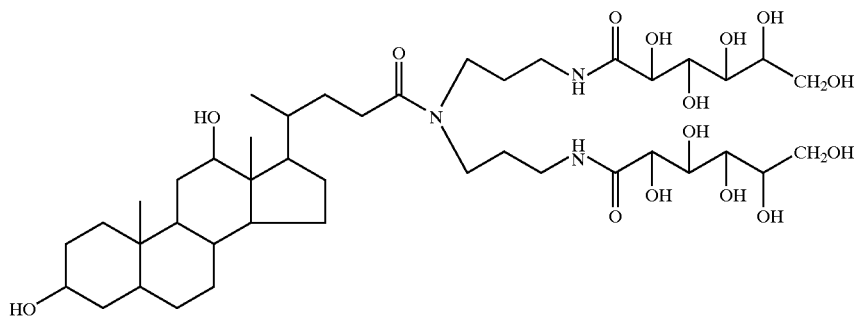

"Deoxy-BIGCHAP";

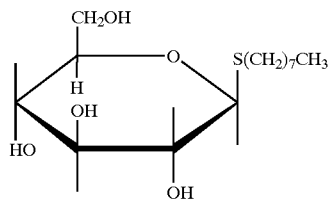

n-octyl-β-D-thioglucoside

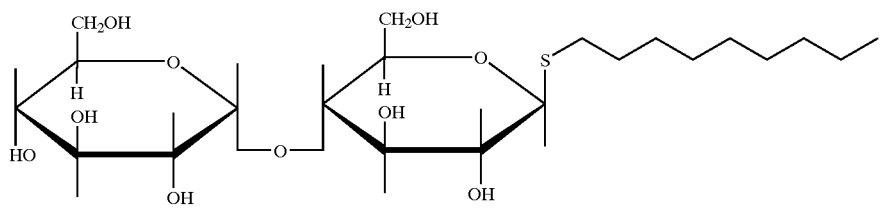

n-nonyl-β-D-thiomaltoside;

-continued

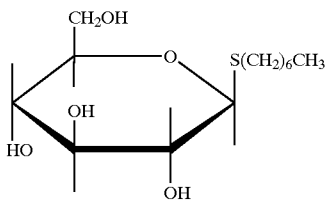

n-heptyl-β-D-thioglucoside;

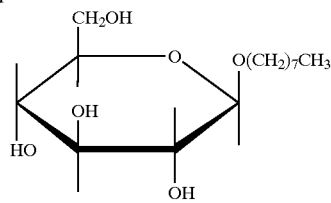

n-octyl-β-D-thioglucoside;

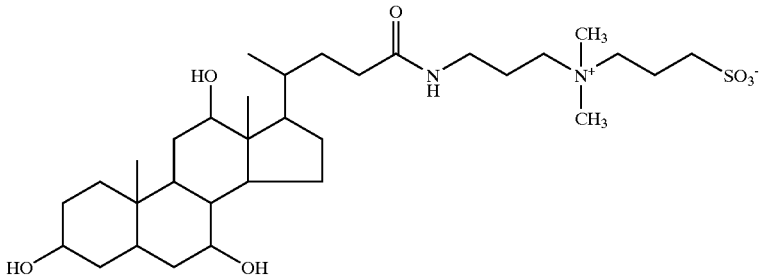

"CHAPS"; and

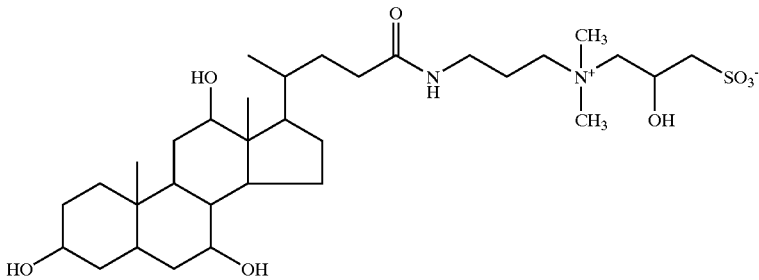

"CHAPSO."

22. A method for discriminating and counting erythroblasts as set forth in claim 21, further comprising the step of flow cytometrically assaying the sample mixed with the hemolytic agent including the surfactant, by measuring the at least one scattered light parameter and at least one fluorescence parameter for discriminating and counting erythroblasts in the body fluid sample by maturation stage.

23. A method for discriminating and counting erythroblasts as set forth in claim 20, wherein the scattered light parameter is at least one selected from low-angle forward scattered light, high-angle forward scattered light, and orthogonal scattered light as a selected angle of scattered light received in the flow cytometric assay.

24. A method for discriminating and counting erythroblasts as set forth in claim 22, wherein at least two erytlroblasts maturation stages are discriminated among erythroblasts in the body fluid sample.

25. A method for discriminating and counting erythroblasts as set forth in claim 20, wherein the body fluid samples are taken from one of the peripheral blood circulation, bone marrow and urine of a human patient.

* * * * *